United States Patent [19]

Tabor et al.

[11] Patent Number: 4,921,794
[45] Date of Patent: May 1, 1990

[54] T7 DNA POLYMERASE

[75] Inventors: Stanley Tabor, Cambridge; Charles C. Richardson, Chestnut Hill, both of Mass.

[73] Assignee: President and Fellows of Harvard College, Cambridge, Mass.

[21] Appl. No.: 279,990

[22] Filed: Dec. 5, 1988

Related U.S. Application Data

[63] Continuation of Ser. No. 3,227, Jan. 14, 1987, Pat. No. 4,795,699.

[51] Int. Cl.[5] .................. C12P 19/34; C12N 15/00; C12N 9/12; C07H 15/12
[52] U.S. Cl. ................................. 435/91; 435/172.3; 435/194; 435/320; 536/27; 935/16; 935/17; 935/18
[58] Field of Search .................. 435/91, 6, 21, 172.3; 935/14, 77, 78

[56] References Cited

U.S. PATENT DOCUMENTS

| | | | |
|---|---|---|---|
| 4,224,408 | 9/1980 | Hung et al. | 435/91 |
| 4,331,589 | 5/1982 | Hung et al. | 260/112 |
| 4,394,443 | 7/1983 | Weissman et al. | 435/6 |
| 4,395,486 | 7/1983 | Wilson et al. | 435/6 |
| 4,555,486 | 11/1985 | Bahl et al. | 435/91 |
| 4,663,290 | 5/1987 | Weis et al. | 435/253 |
| 4,683,195 | 7/1987 | Mullis et al. | 435/91 |
| 4,683,202 | 7/1987 | Mullis | 435/91 |
| 4,767,708 | 8/1988 | Minkley et al. | 435/70 |
| 4,786,600 | 11/1988 | Kramer et al. | 435/235 |
| 4,795,699 | 1/1989 | Tabor et al. | 435/5 |
| 4,800,159 | 1/1989 | Mullis et al. | 435/172.3 |

FOREIGN PATENT DOCUMENTS 0258017 6/1987 European Pat. Off. .

OTHER PUBLICATIONS

Axelrod et al., "Transcription from Bacteriophage T7 and SP6 RNA Polymerase Promoters in the Presence of 3'-Deoxyribonucleoside 5'-Triphosphate Chain Terminators", *Biochemistry*, 24: 5716–5723, 1985.
Hoog et al., "Nucleotide Sequence of the Thioredoxin Gene from *E. coli*", *Bioscience Reports* 4: 917–923, 1984.
Bina-Stein et al., "Rapid Sequence Determination of Late Simian Virus 40, 16S mRNA Leader by Using Inhibitors of Reverse Transcriptase", *Proc. Natl. Acad. Sci.*, USA, 76: 731–745, 1979.
Smith, "DNA Sequence Analysis by Primed Synthesis", *Methods in Enzymology*, vol. 65, pp. 560–580, 1980.
Barrell, "Sequence Analysis of Bacteriophage φX174 DNA", *Biochemistry of Nucleic Acids II*, vol. 17, pp. 125–133, 1978.
Detera et al., "Studies on the Mechanism of *E. coli* DNA Polymerase 1 Large Fragment", *J. Biol. Chem.*, 257: 9770–9780, 1982.
Kornberg, "DNA Replication", W. H. Freeman & Company, pp. 87–100, 116–124, 127–129, 405, 655–661, 1974.
Banker, "Advances in Dideoxy Sequencing", 72 *BioTechniques*, 1984.
Engler, "Bacteriophage T7 DNA Replication", *J. Biol. Chemistry*, 258: 11197, 1983.
Kolodner et al., "Replication of Duplex DNA by Bacteriophage T7 DNA Polymerase and Gene 4 Protein is Accompanied by Hydrolysis of Nucleoside, 5'-triphosphates", *Proc. Natl. Acad. Sci.*, USA, vol. 74, No. 4, pp. 1525–1529 (1977).
Ollis et al., "Domain of *E. coli* DNA Polymerase I Showing Sequence Homology to T7 DNA Polymerase", *Nature*, vol. 313, pp. 818–819, (1985).
Harrison, "Two for the Price of One", *Nature*, vol. 313, 736–737 (1985).
Randall et al., "An Improved Purification Method and a Physical Characterization of Phage T7 DNA Polymerase", *Eur. J. Biochem.*, 128, pp. 445–449 (1982).

Primary Examiner—Thomas D. Mays
Attorney, Agent, or Firm—Fish & Richardson

[57] ABSTRACT

This invention relates to T7-type DNA polymerases and methods for amplification of DNA, for example by polymerase chain reaction.

24 Claims, 17 Drawing Sheets
(List continued on next page.)

OTHER PUBLICATIONS

Nordstrom et al., "Characterization of Bacteriophage T7 DNA Polymerase Purified to Homogeneity by Antithioredoxin Immunoadsorbent Chromatography", Journal of Biological Chemistry, vol. 256, No. 6, pp. 3112–3117 (1981).

Fuller et al., "Initiation of DNA Replication at the Primary Origin of Bacteriophage T7 by Purified Proteins", Journal of Biological Chemistry, vol. 260, No. 5, pp. 3185–3196, 1985.

McClure et al., "the Kinetics and Processivity of Nucleic Acid Polymerases", *Methods in Enzymology*, vol. 64, pp. 277–297, 1980.

Watson et al., "Recombinant DNA", *Cold Spring Harbor*, Laboratory, 1983.

Gregerson et al., "Processive Nature of Reverse Transcription by Avian Myeloblastosis Virus Deoxribonucleic Acid Polymerase", *Biochemistry*, vol. 19, pp. 201–306 (1980).

Kornberg, In *DNA Replication*, W. H. Freeman and Co., pp. 130–134 and 159–166, 1974.

Reutimann et al., "Bacteriophage T7 DNA Polymerase: Cloning and High-Level Expression", Proc. Natl. Acad. Sci., USA, vol. 82: 6783, 1985.

Scharf et al., "Direct Cloning and Sequence Analysis of Enzymatically Amplified Genomic Sequences", Science 233: 1076, 1986.

Saiki et al., "Analysis of Enzymatically Amplified Beta-Globin and HLA-DO Alpha DNA with allele-Specific Oligonucleotide Probes", Nature, 324: 163, 1986.

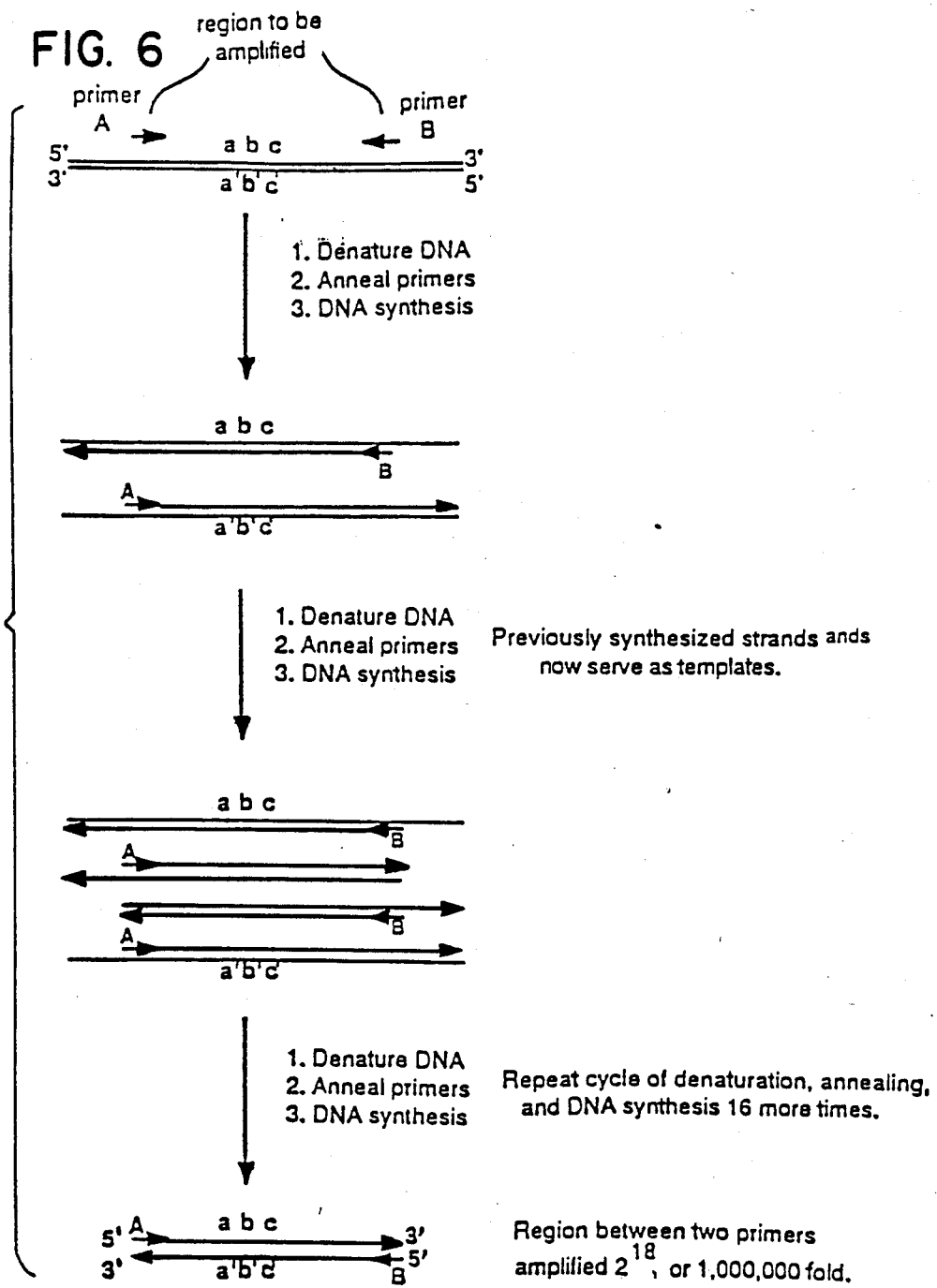

FIG. 7 -1

Nucleotide sequence of: pTrx-2

```
         10         20         30         40         50
  TTCTTCTCAT GTTTGACAGC TTATCATCGA CTGCACGGTG CACCAATGCT
         60         70         80         90        100
  TCTGGCGTCA GGCAGCCATC GGAAGCTGTG GTATGGCTGT GCAGGTCGTA
        110        120        130        140        150
  AATCACTGCA TAATTCGTGT CGCTCAAGGC GCACTCCCGT TCTGGATAAT
        160        170        180        190        200
  GTTTTTTGCG CCGACATCAT AACGGTTCTG GCAAATATTC TGAAATGAGC
        210        220        230        240        250
  TGTTGACAAT TAATCATCGG CTCGTATAAT GTGTGGAATT GTGAGCGGAT
        260        270        280        290        300
  AACAATTTCA CACAGGAAAC AGGGGATCCG TCAACCTTTA GTTGGTTAAT
        310        320        330        340        350
  GTTACACCAA CAACGAAACC AACACGCCAG GCTTATTCCT GTGGAGTTAT
        360        370        380        390        400
  ATATGAGCGA TAAAATTATT CACCTGACTG ACGACAGTTT TGACACGGAT
        410        420        430        440        450
  GTACTCAAAG CGGACGGGGC GATCCTCGTC GATTTCTGGG CAGAGTGGTG
        460        470        480        490        500
  CGGTCCGTGC AAGATGATCG CCCCGATTCT GGATGAAATC GCTGACGAAT
```

FIG. 7 -2

```
          510        520        530        540        550
     ATCAGGGCAA ACTGACCGTT GCAAAACTGA ACATCGATCA AAACCCTGGT
          560        570        580        590        600
     ACTGCGCCGA AATATGGCAT CCGTGGTATC CCGACTCTGC TGCTGTTCAA
          610        620        630        640        650
     AAACGGTGAA GTGGCGGCAA CCAAAGTGGG TGCACTGTCT AAAGGTCAGT
          660       .670        680        690        700
     TGAAAGAGTT CCTCGACGCT AACCTGGCGT AAGGGAATTT CATGTTCGGG
          710        720        730        740        750
     TGCCCCGTCG CTAAAAACTG GACGCCCGGC GTGAGTCATG CTAACTTAGT
          760        770        780        790        800
     GTTGACGGAT CCCCGGGGAT CCGTCAACCT TTAGTTGGTT AATGTTACAC
          810        820        830        840        850
     CAACAACGAA ACCAACACGC CAGGCTTATT CCTGTGGAGT TATATATGAG
          860        870        880        890        900
     CGATAAAATT ATTCACCTGA CTGACGACAG TTTTGACACG GATGTACTCA
          910        920        930        940        950
     AAGCGGACGG GGCGATCCTC GTCGATTTCT GGGCAGAGTG GTGCGGTCCG
          960        970        980        990       1000
     TGCAAGATGA TCGCCCCGAT.TCTGGATGAA ATCGCTGACG AATATCAGGG
         1010       1020       1030       1040       1050
     CAAACTGACC GTTGCAAAAC TGAACATCGA TCAAAACCCT GGTACTGCGC
         1060       1070       1080       1090       1100
     CGAAATATGG CATCCGTGGT ATCCCGACTC TGCTGCTGTT CAAAAACGGT
         1110       1120       1130       1140       1150
     GAAGTGGCGG CAACCAAAGT GGGTGCACTG TCTAAAGGTC AGTTGAAAGA
         1160       1170       1180       1190       1200
     GTTCCTCGAC GCTAACCTGG CGTAAGGGAA TTTCATGTTC GGGTGCCCCG
         1210       1220       1230       1240       1250
     TCGCTAAAAA CTGGACGCCC GGCGTGAGTC ATGCTAACTT AGTGTTGACG
         1260       1270       1280       1290       1300
     GATCCCCCTG CCTCGCGCGT TTCGGTGATG ACGGTGAAAA CCTCTGACAC
         1310       1320       1330       1340       1350
     ATGCAGCTCC CGGAGACGGT CACAGCTTGT CTGTAAGCGG ATGCCGGGAG
         1360       1370       1380       1390       1400
     CAGACAAGCC CGTCAGGGCG CGTCAGCGGG TGTTGGCGGG TGTCGGGGCG
         1410       1420       1430       1440       1450
     CAGCCATGAC CCAGTCACGT AGCGATAGCG GAGTGTATAC TGGCTTAACT
         1460       1470       1480       1490       1500
     ATGCGGCATC AGAGCAGATT GTACTGAGAG TGCACCATAT GCGGTGTGAA
         1510       1520       1530       1540       1550
     ATACCGCACA GATGCGTAAG GAGAAAATAC CGCATCAGGC GCTCTTCCGC
         1560       1570       1580       1590       1600
     TTCCTCGCTC ACTGACTCGC TGCGCTCGGT CGTTCGGCTG CGGCGAGCGG
         1610       1620       1630       1640       1650
     TATCAGCTCA CTCAAAGGCG GTAATACGGT TATCCACAGA ATCAGGGGAT
         1660       1670       1680       1690       1700
     AACGCAGGAA AGAACATGTG AGCAAAAGGC CAGCAAAAGG CCAGGAACCG
         1710       1720       1730       1740       1750
     TAAAAAGGCC GCGTTGCTGG CGTTTTTCCA TAGGCTCCGC CCCCCTGACG
         1760       1770       1780       1790       1800
     AGCATCACAA AAATCGACGC TCAAGTCAGA GGTGGCGAAA CCCGACAGGA
         1810       1820       1830       1840       1850
     CTATAAAGAT ACCAGGCGTT TCCCCCTGGA AGCTCCCTCG TGCGCTCTCC
```

FIG. 7-3

```
          1860       1870       1880       1890       1900
     TGTTCCGACC CTGCCGCTTA CCGGATACCT GTCCGCCTTT CTCCCTTCGG
          1910       1920       1930       1940       1950
     GAAGCGTGGC GCTTTCTCAA TGCTCACGCT GTAGGTATCT CAGTTCGGTG
          1960       1970       1980       1990       2000
     TAGGTCGTTC GCTCCAAGCT GGGCTGTGTG CACGAACCCC CCGTTCAGCC
          2010       2020       2030       2040       2050
     CGACCGCTGC GCCTTATCCG GTAACTATCG TCTTGAGTCC AACCCGGTAA
          2060       2070       2080       2090       2100
     GACACGACTT ATCGCCACTG GCAGCAGCCA CTGGTAACAG GATTAGCAGA
          2110       2120       2130       2140       2150
     GCGAGGTATG TAGGCGGTGC TACAGAGTTC TTGAAGTGGT GGCCTAACTA
          2160       2170       2180       2190       2200
     CGGCTACACT AGAAGGACAG TATTTGGTAT CTGCGCTCTG CTGAAGCCAG
          2210       2220       2230       2240       2250
     TTACCTTCGG AAAAGAGTT GGTAGCTCTT GATCCGGCAA ACAAACCACC
          2260       2270       2280       2290       2300
     GCTGGTAGCG GTGGTTTTTT TGTTTGCAAG CAGCAGATTA CGCGCAGAAA
          2310       2320       2330       2340       2350
     AAAAGGATCT CAAGAAGATC CTTTGATCTT TTCTACGGGG TCTGACGCTC
          2360       2370       2380       2390       2400
     AGTGGAACGA AAACTCACGT TAAGGGATTT TGGTCATGAG ATTATCAAAA
          2410       2420       2430       2440       2450
     AGGATCTTCA CCTAGATCCT TTTAAATTAA AAATGAAGTT TTAAATCAAT
          2460       2470       2480       2490       2500
     CTAAAGTATA TATGAGTAAA CTTGGTCTGA CAGTTACCAA TGCTTAATCA
          2510       2520       2530       2540       2550
     GTGAGGCACC TATCTCAGCG ATCTGTCTAT TTCGTTCATC CATAGTTGCC
          2560       2570       2580       2590       2600
     TGACTCCCCG TCGTGTAGAT AACTACGATA CGGGAGGGCT TACCATCTGG
          2610       2620       2630       2640       2650
     CCCCAGTGCT GCAATGATAC CGCGAGACCC ACGCTCACCG GCTCCAGATT
          2660       2670       2680       2690       2700
     TATCAGCAAT AAACCAGCCA GCCGGAAGGG CCGAGCGCAG AAGTGGTCCT
          2710       2720       2730       2740       2750
     GCAACTTTAT CCGCCTCCAT CCAGTCTATT AATTGTTGCC GGGAAGCTAG
          2760       2770       2780       2790       2800
     AGTAAGTAGT TCGCCAGTTA ATAGTTTGCG CAACGTTGTT GCCATTGCTG
          2810       2820       2830       2840       2850
     CAGGCATCGT GGTGTCACGC TCGTCGTTTG GTATGGCTTC ATTCAGCTCC
          2860       2870       2880       2890       2900
     GGTTCCCAAC GATCAAGGCG AGTTACATGA TCCCCCATGT TGTGCAAAAA
          2910       2920       2930       2940       2950
     AGCGGTTAGC TCCTTCGGTC CTCCGATCGT TGTCAGAAGT AAGTTGGCCG
          2960       2970       2980       2990       3000
     CAGTGTTATC ACTCATGGTT ATGGCAGCAC TGCATAATTC TCTTACTGTC
          3010       3020       3030       3040       3050
     ATGCCATCCG TAAGATGCTT TTCTGTGACT GGTGAGTACT CAACCAAGTC
          3060       3070       3080       3090       3100
     ATTCTGAGAA TAGTGTATGC GGCGACCGAG TTGCTCTTGC CCGGCGTCAA
          3110       3120       3130       3140       3150
     CACGGGATAA TACCGCGCCA CATAGCAGAA CTTTAAAAGT GCTCATCATT
          3160       3170       3180       3190       3200
     GGAAAACGTT CTTCGGGGCG AAAACTCTCA AGGATCTTAC CGCTGTTGAG
```

FIG. 7-4

```
     3210       3220       3230       3240       3250
ATCCAGTTCG ATGTAACCCA CTCGTGCACC CAACTGATCT TCAGCATCTT
     3260       3270       3280       3290       3300
TTACTTTCAC CAGCGTTTCT GGGTGAGCAA AAACAGGAAG GCAAAATGCC
     3310       3320       3330       3340       3350
GCAAAAAAGG GAATAAGGGC GACACGGAAA TGTTGAATAC TCATACTCTT
     3360       3370       3380       3390       3400
CCTTTTTCAA TATTATTGAA GCATTTATCA GGGTTATTGT CTCATGAGCG
     3410       3420       3430       3440       3450
GATACATATT TGAATGTATT TAGAAAAATA AACAAATAGG GGTTCCGCGC
     3460       3470       3480       3490       3500
ACATTCCCC GAAAAGTGCC ACCTGACGTC TAAGAAACCA TTATTATCAT
     3510       3520       3530       3540       3550
GACATTAACC TATAAAAATA GGCGTATCAC GAGGCCCTTT CGTCTTCAAG
```

Nucleotide sequence of: pGP5-5

```
          10         20         30         40         50
    GTTGACACAT ATGAGTCTTG TGATGTACTG GCTGATTTCT ACGACCAGTT
          60         70         80         90        100
    CGCTGACCAG TTGCACGAGT CTCAATTGGA CAAAATGCCA GCACTTCCGG
         110        120        130        140        150
    CTAAAGGTAA CTTGAACCTC CGTGACATCT TAGAGTCGGA CTTCGCGTTC
         160        170        180        190        200
    GCGTAACGCC AAATCAATAC GACTCACTAT AGAGGGACAA ACTCAAGGTC
         210        220        230        240        250
    ATTCGCAAGA GTGGCCTTTA TGATTGACCT TCTTCCGGTT AATACGACTC
         260        270        280        290        300
    ACTATAGGAG AACCTTAAGG TTTAACTTTA AGACCCTTAA GTGTTAATTA
         310        320        330        340        350
    GAGATTTAAA TTAAAGAATT ACTAAGAGAG GACTTTAAGT ATGCGTAACT
         360        370        380        390        400
    TCGAAAAGAT GACCAAACGT TCTAACCGTA ATGCTCGTGA CTTCGAGGCA
         410        420        430        440        450
    ACCAAAGGTC GCAAGTTGAA TAAGACTAAG CGTGACCGCT CTCACAAGCG
         460        470        480        490        500
    TAGCTGGGAG GGTCAGTAAG ATGGGACGTT TATATAGTGG TAATCTGGCA
         510        520        530        540        550
    CCGGATCCGG TATGAAGAGA TTGTTAAGTC ACGATAATCA ATAGGAGAAA
         560        570        580        590        600
    TCAATATGAT CGTTTCTGAC ATCGAAGCTA ACGCCCTCTT AGAGAGCGTC
```

FIG. 8-2

```
          610        620        630        640        650
     ACTAAGTTCC ACTGCGGGGT TATCTACGAC TACTCCACCG CTGAGTACGT
          660        670        680        690        700
     AAGCTACCGT CCGAGTGACT TCGGTGCGTA TCTGGATGCG CTGGAAGCCG
          710        720        730        740        750
     AGGTTGCACG AGGCGGTCTT ATTGTGTTCC ACAACGGTCA CAAGTATGAC
          760        770        780        790        800
     GTTCCTGCAT TGACCAAACT GGCAAAGTTG CAATTGAACC GAGAGTTCCA
          810        820        830        840        850
     CCTTCCTCGT GAGAACTGTA TTGACACCCT TGTGTTGTCA CGTTTGATTC
          860        870        880        890        900
     ATTCCAACCT CAAGGACACC GATATGGGTC TTCTGCGTTC CGGCAAGTTG
          910        920        930        940        950
     CCCGGAAAAC GCTTTGGGTC TCACGCTTTG GAGGCGTGGG GTTATCGCTT
          960        970        980        990       1000
     AGGCGAGATG AAGGGTGAAT ACAAAGACGA CTTTAAGCGT ATGCTTGAAG
         1010       1020       1030       1040       1050
     AGCAGGGTGA AGAATACGTT GACGGAATGG AGTGGTGGAA CTTCAACGAA
         1060       1070       1080       1090       1100
     GAGATGATGG ACTATAACGT TCAGGACGTT GTGGTAACTA AAGCTCTCCT
         1110       1120       1130       1140       1150
     TGAGAAGCTA CTCTCTGACA AACATTACTT CCCTCCTGAG ATTGACTTTA
         1160       1170       1180       1190       1200
     CGGACGTAGG ATACACTACG TTCTGGTCAG AATCCCTTGA GGCCGTTGAC
         1210       1220       1230       1240       1250
     ATTGAACATC GTGCTGCATG GCTGCTCGCT AAACAAGAGC GCAACGGGTT
         1260       1270       1280       1290       1300
     CCCGTTTGAC ACAAAAGCAA TCGAAGAGTT GTACGTAGAG TTAGCTGCTC
         1310       1320       1330       1340       1350
     GCCGCTCTGA GTTGCTCCGT AAATTGACCG AAACGTTCGG CTCGTGGTAT
         1360       1370       1380       1390       1400
     CAGCCTAAAG GTGGCACTGA GATGTTCTGC CATCCGCGAA CAGGTAAGCC
         1410       1420       1430       1440       1450
     ACTACCTAAA TACCCTCGCA TTAAGACACC TAAAGTTGGT GGTATCTTTA
         1460       1470       1480       1490       1500
     AGAAGCCTAA GAACAAGGCA CAGCGAGAAG GCCGTGAGCC TTGCGAACTT
         1510       1520       1530       1540       1550
     GATACCCGCG AGTACGTTGC TGGTGCTCCT TACACCCCAG TTGAACATGT
         1560       1570       1580       1590       1600
     TGTGTTTAAC CCTTCGTCTC GTGACCACAT TCAGAAGAAA CTCCAAGAGG
         1610       1620       1630       1640       1650
     CTGGGTGGGT CCCGACCAAG TACACCGATA AGGGTGCTCC TGTGGTGGAC
         1660       1670       1680       1690       1700
     GATGAGGTAC TCGAAGGAGT ACGTGTAGAT GACCCTGAGA AGCAAGCCGC
         1710       1720       1730       1740       1750
     TATCGACCTC ATTAAAGAGT ACTTGATGAT TCAGAAGCGA ATCGGACAGT
         1760       1770       1780       1790       1800
     CTGCTGAGGG AGACAAAGCA TGGCTTCGTT ATGTTGCTGA GGATGGTAAG
         1810       1820       1830       1840       1850
     ATTCATGGTT CTGTTAACCC TAATGGAGCA GTTACGGGTC GTGCGACCCA
         1860       1870       1880       1890       1900
     TGCGTTCCCA AACCTTGCGC AAATTCCGGG TGTACGTTCT CCTTATGGAG
         1910       1920       1930       1940       1950
     AGCAGTGTCG CGCTGCTTTT GGCGCTGAGC ACCATTTGGA TGGGATAACT
```

FIG. 8-3

```
           1960        1970       1980       1990       2000
       GGTAAGCCTT GGGTTCAGGC TGGCATCGAC GCATCCGGTC TTGAGCTACG
           2010        2020       2030       2040       2050
       CTGCTTGGCT CACTTCATGG CTCGCTTTGA TAACGGCGAG TACGCTCACG
           2060        2070       2080       2090       2100
       AGATTCTTAA CGGCGACATC CACACTAAGA ACCAGATAGC TGCTGAACTA
           2110        2120       2130       2140       2150
       CCTACCCGAG ATAACGCTAA GACGTTCATC TATGGGTTCC TCTATGGTGC
           2160        2170       2180       2190       2200
       TGGTGATGAG AAGATTGGAC AGATTGTTGG TGCTGGTAAA GAGCGCGGTA
           2210        2220       2230       2240       2250
       AGGAACTCAA GAAGAAATTC CTTGAGAACA CCCCCGCGAT TGCAGCACTC
           2260        2270       2280       2290       2300
       CGCGAGTCTA TCCAACAGAC ACTTGTCGAG TCCTCTCAAT GGGTAGCTGG
           2310        2320       2330       2340       2350
       TGAGCAACAA GTCAAGTGGA AACGCCGCTG GATTAAAGGT CTGGATGGTC
           2360        2370       2380       2390       2400
       GTAAGGTACA CGTTCGTAGT CCTCACGCTG CCTTGAATAC CCTACTGCAA
           2410        2420       2430.      2440       2450
       TCTGCTGGTG CTCTCATCTG CAAACTGTGG ATTATCAAGA CCGAAGAGAT
           2460        2470       2480       2490       2500
       GCTCGTAGAG AAAGGCTTGA AGCATGGCTG GGATGGGGAC TTTGCGTACA
           2510        2520       2530       2540       2550
       TGGCATGGGT ACATGATGAA ATCCAAGTAG GCTGCCGTAC CGAAGAGATT
           2560        2570       2580       2590       2600
       GCTCAGGTGG TCATTGAGAC CGCACAAGAA GCGATGCGCT GGGTTGGAGA
           2610        2620       2630       2640       2650
       CCACTGGAAC TTCCGGTGTC TTCTGGATAC CGAAGGTAAG ATGGGTCCTA
           2660        2670       2680       2690       2700
       ATTGGGCGAT TTGCCACTGA TACAGGAGGC TACTCATGAA CGAAAGACAC
           2710        2720       2730       2740       2750
       TTAACAGGTG CTGCTTCTGA AATGCTAGTA GCCTACAAAT TTACCAAAGC
           2760        2770       2780       2790       2800
       TGGGTACACT GTCTATTACC CTATGCTGAC TCAGAGTAAA GAGGACTTGG
           2810        2820       2830       2840       2850
       TTGTATGTAA GGATGGTAAA TTTAGTAAGG TTCAGGTTAA AACAGCCACA
           2860        2870       2880       2890       2900
       ACGGTTCAAA CCAACACAGG AGATGCCAAG CAGGTTAGGC TAGGTGGATG
           2910        2920       2930       2940       2950
       CGGTAGGTCC GAATATAAGG ATGGAGACTT TGACATTCTT GCGGTTGTGG
           2960        2970       2980       2990       3000
       TTGACGAAGA TGTGCTTATT TTCACATGGG ACGAAGTAAA AGGTAAGACA
           3010        3020       3030       3040       3050
       TCCATGTGTG TCGGCAAGAG AAACAAAGGC ATAAAACTAT AGGAGAAATT
           3060        3070       3080
       ATTATGGCTA TGACAAAGAA ATTTCCGGAT C
```

FIG. 9-1

Nucleotide sequence of: mGP1-2

```
          10         20         30         40         50
   AATGCTACTA CTATTAGTAG AATTGATGCC ACCTTTTCAG CTCGCGCCCC
          60         70         80         90        100
   AAATGAAAAT ATAGCTAAAC AGGTTATTGA CCATTTGCGA AATGTATCTA
         110        120        130        140        150
   ATGGTCAAAC TAAATCTACT CGTTCGCAGA ATTGGGAATC AACTGTTACA
         160        170        180        190        200
   TGGAATGAAA CTTCCAGACA CCGTACTTTA GTTGCATATT TAAAACATGT
         210        220        230        240        250
   TGAGCTACAG CACCAGATTC AGCAATTAAG CTCTAAGCCA TCCGCAAAAA
         260        270        280        290        300
   TGACCTCTTA TCAAAAGGAG CAATTAAAGG TACTCTCTAA TCCTGACCTG
         310        320        330        340        350
   TTGGAGTTTG CTTCCGGTCT GGTTCGCTTT GAAGCTCGAA TTAAAACGCG
         360        370        380        390        400
   ATATTTGAAG TCTTTCGGGC TTCCTCTTAA TCTTTTTGAT GCAATCCGCT
         410        420        430        440        450
   TTGCTTCTGA CTATAATAGT CAGGGTAAAG ACCTGATTTT TGATTTATGG
         460        470        480        490        500
   TCATTCTCGT TTTCTGAACT GTTTAAAGCA TTTGAGGGGG ATTCAATGAA
         510        520        530        540        550
   TATTTATGAC GATTCCGCAG TATTGGACGC TATCCAGTCT AAACATTTTA
         560        570        580        590        600
   CTATTACCCC CTCTGGCAAA ACTTCTTTTG CAAAAGCCTC TCGCTATTTT
         610        620        630        640        650
   GGTTTTTATC GTCGTCTGGT AAACGAGGGT TATGATAGTG TTGCTCTTAC
         660        670        680        690        700
   TATGCCTCGT AATTCCTTTT GGCGTTATGT ATCTGCATTA GTTGAATGTG
         710        720        730        740        750
   GTATTCCTAA ATCTCAACTG ATGAATCTTT CTACCTGTAA TAATGTTGTT
         760        770        780        790        800
   CCGTTAGTTC GTTTTATTAA CGTAGATTTT TCTTCCCAAC GTCCTGACTG
         810        820        830        840        850
   GTATAATGAG CCAGTTCTTA AAATCGCATA AGGTAATTCA CAATGATTAA
         860        870        880        890        900
```

FIG. 9-2

```
AGTTGAAATT AAACCATCTC AAGCCCAATT TACTACTCGT TCTGGTGGTT
   910        920        930        940        950
CTCGTCAGGG CAAGCCTTAT TCACTGAATG AGCAGCTTTG TTACGTTGAT
   960        970        980        990       1000
TTGGGTAATG AATATCCGGT TCTTGTCAAG ATTACTCTTG ATGAAGGTCA
  1010       1020       1030       1040       1050
GCCAGCCTAT GCGCCTGGTC TGTACACCGT TCATCTGTCC TCTTTCAAAG
  1060       1070       1080       1090       1100
TTGGTCAGTT CGGTTCCCTT ATGATTGACC GTCTGCGCCT CGTTCCGGCT
  1110       1120       1130       1140       1150
AAGTAACATG GAGCAGGTCG CGGATTTCGA CACAATTTAT CAGGCGATGA
  1160       1170       1180       1190       1200
TACAAATCTC CGTTGTACTT TGTTTCGCGC TTGGTATAAT CGCTGGGGGT
  1210       1220       1230       1240       1250
CAAAGATGAG TGTTTTAGTG TATTCTTTCG CCTCTTTCGT TTTAGGTTGG
  1260       1270       1280       1290       1300
TGCCTTCGTA GTGGCATTAC GTATTTACC CGTTTAATGC AAACTTCCTC
  1310       1320       1330       1340       1350
ATGAAAAAGT CTTTAGTCCT CAAAGCCTCT GTAGCCGTTG CTACCCTCGT
  1360       1370       1380       1390       1400
TCCGATGCTG TCTTTCGCTG CTGAGGGTGA CGATCCCGCA AAAGCGGCCT
  1410       1420       1430       1440       1450
TTAACTCCCT GCAAGCCTCA GCGACCGAAT ATATCGGTTA TGCGTGGGCG
  1460       1470       1480       1490       1500
ATGGTTGTTG TCATTGTCGG CGCAACTATC GGTATCAAGC TGTTTAAGAA
  1510       1520       1530       1540       1550
ATTCACCTCG AAAGCAAGCT GATAAACCGA TACAATTAAA GGCTCCTTTT
  1560       1570       1580       1590       1600
GGAGCCTTTT TTTTTGGAGA TTTTCAACGT GAAAAAATTA TTATTCGCAA
  1610       1620       1630       1640       1650
TTCCTTTAGT TGTTCCTTTC TATTCTCACT CCGCTGAAAC TGTTGAAAGT
  1660       1670       1680       1690       1700
TGTTTAGCAA AACCCCATAC AGAAAATTCA TTTACTAACG TCTGGAAAGA
  1710       1720       1730       1740       1750
CGACAAAACT TTAGATCGTT ACGCTAACTA TGAGGGTTGT CTGTGGAATG
  1760       1770       1780       1790       1800
CTACAGGCGT TGTAGTTTGT ACTGGTGACG AAACTCAGTG TTACGGTACA
  1810       1820       1830       1840       1850
TGGGTTCCTA TTGGGCTTGC TATCCCTGAA AATGAGGGTG GTGGCTCTGA
  1860       1870       1880       1890       1900
GGGTGGCGGT TCTGAGGGTG GCGGTTCTGA GGGTGGCGGT ACTAAACCTC
  1910       1920       1930       1940       1950
CTGAGTACGG TGATACACCT ATTCCGGGCT ATACTTATAT CAACCCTCTC
  1960       1970       1980       1990       2000
GACGGCACTT ATCCGCCTGG TACTGAGCAA AACCCCGCTA ATCCTAATCC
  2010       2020       2030       2040       2050
TTCTCTTGAG GAGTCTCAGC CTCTTAATAC TTTCATGTTT CAGAATAATA
  2060       2070       2080       2090       2100
GGTTCCGAAA TAGGCAGGGG GCATTAACTG TTTATACGGG CACTGTTACT
  2110       2120       2130       2140       2150
CAAGGCACTG ACCCCGTTAA AACTTATTAC CAGTACACTC CTGTATCATC
  2160       2170       2180       2190       2200
AAAAGCCATG TATGACGCTT ACTGGAACGG TAAATTCAGA GACTGCGCTT
  2210       2220       2230       2240       2250
```

FIG. 9-3

```
TCCATTCTGG CTTTAATGAA GATCCATTCG TTTGTGAATA TCAAGGCCAA
    2260       2270       2280       2290       2300
TCGTCTGACC TGCCTCAACC TCCTGTCAAT GCTGGCGGCG GCTCTGGTGG
    2310       2320       2330       2340       2350
TGGTTCTGGT GGCGGCTCTG AGGGTGGTGG CTCTGAGGGT GGCGGTTCTG
    2360       2370       2380       2390       2400
AGGGTGGCGG CTCTGAGGGA GGCGGTTCCG GTGGTGGCTC TGGTTCCGGT
    2410       2420       2430       2440       2450
GATTTTGATT ATGAAAAGAT GGCAAACGCT AATAAGGGGG CTATGACCGA
    2460       2470       2480       2490       2500
AAATGCCGAT GAAAACGCGC TACAGTCTGA CGCTAAAGGC AAACTTGATT
    2510       2520       2530       2540       2550
CTGTCGCTAC TGATTACGGT GCTGCTATCG ATGGTTTCAT TGGTGACGTT
    2560       2570       2580       2590       2600
TCCGGCCTTG CTAATGGTAA TGGTGCTACT GGTGATTTTG CTGGCTCTAA
    2610       2620       2630       2640       2650
TTCCCAAATG GCTCAAGTCG GTGACGGTGA TAATTCACCT TTAATGAATA
    2660       2670       2680       2690       2700
ATTTCCGTCA ATATTTACCT TCCCTCCCTC AATCGGTTGA ATGTCGCCCT
    2710       2720       2730       2740       2750
TTTGTCTTTA GCGCTGGTAA ACCATATGAA TTTTCTATTG ATTGTGACAA
    2760       2770       2780       2790       2800
AATAAACTTA TTCCGTGGTG TCTTTGCGTT TCTTTTATAT GTTGCCACCT
    2810       2820       2830       2840       2850
TTATGTATGT ATTTTCTACG TTTGCTAACA TACTGCGTAA TAAGGAGTCT
    2860       2870       2880       2890       2900
TAATCATGCC AGTTCTTTTG GGTATTCCGT TATTATTGCG TTTCCTCGGT
    2910       2920       2930       2940       2950
TTCCTTCTGG TAACTTTGTT CGGCTATCTG CTTACTTTTC TTAAAAAGGG
    2960       2970       2980       2990       3000
CTTCGGTAAG ATAGCTATTG CTATTTCATT GTTTCTTGCT CTTATTATTG
    3010       3020       3030       3040       3050
GGCTTAACTC AATTCTTGTG GGTTATCTCT CTGATATTAG CGCTCAATTA
    3060       3070       3080       3090       3100
CCCTCTGACT TTGTTCAGGG TGTTCAGTTA ATTCTCCCGT CTAATGCGCT
    3110       3120       3130       3140       3150
TCCCTGTTTT TATGTTATTC TCTCTGTAAA GGCTGCTATT TTCATTTTTG
    3160       3170       3180       3190       3200
ACGTTAAACA AAAAATCGTT TCTTATTTGG ATTGGGATAA ATAATATGGC
    3210       3220       3230       3240       3250
TGTTTATTTT GTAACTGGCA AATTAGGCTC TGGAAAGACG CTCGTTAGCG
    3260       3270       3280       3290       3300
TTGGTAAGAT TCAGGATAAA ATTGTAGCTG GGTGCAAAAT AGCAACTAAT
    3310       3320       3330       3340       3350
CTTGATTTAA GGCTTCAAAA CCTCCCGCAA GTCGGGAGGT TCGCTAAAAC
    3360       3370       3380       3390       3400
GCCTCGCGTT CTTAGAATAC CGGATAAGCC TTCTATATCT GATTTGCTTG
    3410       3420       3430       3440       3450
CTATTGGGCG CGGTAATGAT TCCTACGATG AAAATAAAAA CGGCTTGCTT
    3460       3470       3480       3490       3500
GTTCTCGATG AGTGCGGTAC TTGGTTTAAT ACCCGTTCTT GGAATGATAA
    3510       3520       3530       3540       3550
GGAAAGACAG CCGATTATTG ATTGGTTTCT ACATGCTCGT AAATTAGTAT
    3560       3570       3580       3590       3600
```

FIG. 9-4

```
GGGATATTAT TTTTCTTGTT CAGGACTTAT CTATTGTTGA TAAACAGGCG
    3610       3620       3630       3640       3650
CGTTCTGCAT TAGCTGAACA TGTTGTTTAT TGTCGTCGTC TGGACAGAAT
    3660       3670       3680       3690       3700
TACTTTACCT TTTGTCGGTA CTTTATATTC TCTTATTACT GGCTCGAAAA
    3710       3720       3730       3740       3750
TGCCTCTGCC TAAATTACAT GTTGGCGTTG TTAAATATGG CGATTCTCAA
    3760       3770       3780       3790       3800
TTAAGCCCTA CTGTTGAGCG TTGGCTTTAT ACTGGTAAGA ATTTGTATAA
    3810       3820       3830       3840       3850
CGCATATGAT ACTAAACAGG CTTTTTCTAG TAATTATGAT TCCGGTGTTT
    3860       3870       3880       3890       3900
ATTCTTATTT AACGCCTTAT TTATCACACG GTCGGTATTT CAAACCATTA
    3910       3920       3930       3940       3950
AATTTAGGTC AGAAGATGAA ATTAACTAAA ATATATTTGA AAAAGTTTTC
    3960       3970       3980       3990       4000
TCGCGTTCTT TGTCTTGCGA TTGGATTTGC ATCAGCATTT ACATATAGTT
    4010       4020       4030       4040       4050
ATATAACCCA ACCTAAGCCG GAGGTTAAAA AGGTAGTCTC TCAGACCTAT
    4060       4070       4080       4090       4100
GATTTTGATA AATTCACTAT TGACTCTTCT CAGCGTCTTA ATCTAAGCTA
    4110       4120       4130       4140       4150
TCGCTATGTT TTCAAGGATT CTAAGGGAAA ATTAATTAAT AGCGACGATT
    4160       4170       4180       4190       4200
TACAGAAGCA AGGTTATTCA CTCACATATA TTGATTTATG TACTGTTTCC
    4210       4220       4230       4240       4250
ATTAAAAAAG GTAATTCAAA TGAAATTGTT AAATGTAATT AATTTTGTTT
    4260       4270       4280       4290       4300
TCTTGATGTT TGTTTCATCA TCTTCTTTTG CTCAGGTAAT TGAAATGAAT
    4310       4320       4330       4340       4350
AATTCGCCTC TGCGCGATTT TGTAACTTGG TATTCAAAGC AATCAGGCGA
    4360       4370       4380       4390       4400
ATCCGTTATT GTTTCTCCCG ATGTAAAAGG TACTGTTACT GTATATTCAT
    4410       4420       4430       4440       4450
CTGACGTTAA ACTTGAAAAT CTACGCAATT TCTTTATTTC TGTTTTACGT
    4460       4470       4480       4490       4500
GCTAATAATT TTGATATGGT TGGTTCAATT CCTTCCATAA TTCAGAAGTA
    4510       4520       4530       4540       4550
TAATCCAAAC AATCAGGTAT ATATTGATGA ATTGCCATCA TCTGATAATC
    4560       4570       4580       4590       4600
AGGAATATGA TGATAATTCC GCTCCTTCTG GTGGTTTCTT TGTTCCGCAA
    4610       4620       4630       4640       4650
AATGATAATG TTACTCAAAC TTTTAAAATT AATAACGTTC GGGCAAAGGA
    4660       4670       4680       4690       4700
TTTAATACGA GTTGTCGAAT TGTTTGTAAA GTCTAATACT TCTAAATCCT
    4710       4720       4730       4740       4750
CAAATGTATT ATCTATTGAC GGCTCTAATC TATTAGTTGT TAGTGCACCT
    4760       4770       4780       4790       4800
AAAGATATTT TAGATAACCT TCCTCAATTC CTTTCTACTG TTGATTTGCC
    4810       4820       4830       4840       4850
AACTGACCAG ATATTGATTG AGGGTTTGAT ATTTGAGGTT CAGCAAGGTG
    4860       4870       4880       4890       4900
ATGCTTTAGA TTTTTCATTT GCTGCTGGCT CTCAGCGTGG CACTGTTGCA
    4910       4920       4930       4940       4950
```

FIG. 9-5

```
GGCGGTGTTA ATACTGACCG CCTCACCTCT GTTTTATCTT CTGCTGGTGG
    4960       4970       4980       4990       5000
TTCGTTCGGT ATTTTTAATG GCGATGTTTT AGGGCTATCA GTTCGCGCAT
    5010       5020       5030       5040       5050
TAAAGACTAA TAGCCATTCA AAAATATTGT CTGTGCCACG TATTCTTACG
    5060       5070       5080       5090       5100
CTTTCAGGTC AGAAGGGTTC TATCTCTGTT GGCCAGAATG TCCCTTTTAT
    5110       5120       5130       5140       5150
TACTGGTCGT GTGACTGGTG AATCTGCCAA TGTAAATAAT CCATTTCAGA
    5160       5170       5180       5190       5200
CGATTGAGCG TCAAAATGTA GGTATTTCCA TGAGCGTTTT TCCTGTTGCA
    5210       5220       5230       5240       5250
ATGGCTGGCG GTAATATTGT TCTGGATATT ACCAGCAAGG CCGATAGTTT
    5260       5270       5280       5290       5300
GAGTTCTTCT ACTCAGGCAA GTGATGTTAT TACTAATCAA AGAAGTATTG
    5310       5320       5330       5340       5350
CTACAACGGT TAATTTGCGT GATGGACAGA CTCTTTTACT CGGTGGCCTC
    5360       5370       5380       5390       5400
ACTGATTATA AAAACACTTC TCAAGATTCT GGCGTACCGT TCCTGTCTAA
    5410       5420       5430       5440       5450
AATCCCTTTA ATCGGCCTCC TGTTTAGCTC CCGCTCTGAT TCCAACGAGG
    5460       5470       5480       5490       5500
AAAGCACGTT ATACGTGCTC GTCAAAGCAA CCATAGTACG CGCCCTGTAG
    5510       5520       5530       5540       5550
CGGCGCATTA AGCGCGGCGG GTGTGGTGGT TACGCGCAGC GTGACCGCTA
    5560       5570       5580       5590       5600
CACTTGCCAG CGCCCTAGCG CCCGCTCCTT TCGCTTTCTT CCCTTCCTTT
    5610       5620       5630       5640       5650
CTCGCCACGT TCGCCGGCTT TCCCCGTCAA GCTCTAAATC GGGGGCTCCC
    5660       5670       5680       5690       5700
TTTAGGGTTC CGATTTAGTG CTTTACGGCA CCTCGACCCC AAAAAACTTG
    5710       5720       5730       5740       5750
ATTTGGGTGA TGGTTCACGT AGTGGGCCAT CGCCCTGATA GACGGTTTTT
    5760       5770       5780       5790       5800
CGCCCTTTGA CGTTGGAGTC CACGTTCTTT AATAGTGGAC TCTTGTTCCA
    5810       5820       5830       5840       5850
AACTGGAACA ACACTCAACC CTATCTCGGG CTATTCTTTT GATTTATAAG
    5860       5870       5880       5890       5900
GGATTTTGCC GATTTCGGAA CCACCATCAA ACAGGATTTT CGCCTGCTGG
    5910       5920       5930       5940       5950
GGCAAACCAG CGTGGACCGC TTGCTGCAAC TCTCTCAGGG CCAGGCGGTG
    5960       5970       5980       5990       6000
AAGGGCAATC AGCTGTTGCC CGTCTCGCTG GTGAAAAGAA AAACCACCCT
    6010       6020       6030       6040       6050
GGCGCCCAAT ACGCAAACCG CCTCTCCCCG CGCGTTGGCC GATTCATTAA
    6060       6070       6080       6090       6100
TCCAGCTGGC ACGACAGGTT TCCCGACTGG AAAGCGGGCA GTGAGCGCAA
    6110       6120       6130       6140       6150
CGCAATTAAT GTGAGTTACC TCACTCATTA GGCACCCCAG GCTTTACACT
    6160       6170       6180       6190       6200
TTATGCTTCC GGCTCGTATG TTGTGTGGAA TTGTGAGCGG ATAACAATTT
    6210       6220       6230       6240       6250
CACACAGGAA ACAGCTATGA CCATGATTAC GAATTCGAGC TCGCCCGGGG
    6260       6270       6280       6290       6300
```

FIG. 9-6

```
ATCTGCCTGA ATAGGTACGA TTTACTAACT GGAAGAGGCA CTAAATGAAC
    6310       6320       6330       6340       6350
ACGATTAACA TCGCTAAGAA CGACTTCTCT GACATCGAAC TGGCTGCTAT
    6360       6370.      6380       6390       6400
CCCGTTCAAC ACTCTGGCTG ACCATTACGG TGAGCGTTTA GCTCGCGAAC
    6410       6420       6430       6440       6450
AGTTGGCCCT TGAGCATGAG TCTTACGAGA TGGGTGAAGC ACGCTTCCGC
    6460       6470       6480       6490       6500
AAGATGTTTG AGCGTCAACT TAAAGCTGGT GAGGTTGCGG ATAACGCTGC
    6510       6520       6530       6540       6550
CGCCAAGCCT CTCATCACTA CCCTACTCCC TAAGATGATT GCACGCATCA
    6560       6570       6580       6590       6600
ACGACTGGTT TGAGGAAGTG AAAGCTAAGC GCGGCAAGCG CCCGACAGCC
    6610       6620       6630       6640       6650
TTCCAGTTCC TGCAAGAAAT CAAGCCGGAA GCCGTAGCGT ACATCACCAT
    6660       6670       6680       6690       6700
TAAGACCACT CTGGCTTGCC TAACCAGTGC TGACAATACA ACCGTTCAGG
    6710       6720       6730       6740       6750
CTGTAGCAAG CGCAATCGGT CGGGCCATTG AGGACGAGGC TCGCTTCGGT
    6760       6770       6780       6790       6800
CGTATCCGTG ACCTTGAAGC TAAGCACTTC AAGAAAAACG TTGAGGAACA
    6810       6820       6830       6840       6850
ACTCAACAAG CGCGTAGGGC ACGTCTACAA GAAAGCATTT ATGCAAGTTG
    6860       6870       6880       6890       6900
TCGAGGCTGA CATGCTCTCT AAGGGTCTAC TCGGTGGCGA GGCGTGGTCT
    6910       6920       6930       6940       6950
TCGTGGCATA AGGAAGACTC TATTCATGTA GGAGTACGCT GCATCGAGAT
    6960       6970       6980       6990       7000
GCTCATTGAG TCAACCGGAA TGGTTAGCTT ACACCGCCAA AATGCTGGCG
    7010       7020       7030       7040       7050
TAGTAGGTCA AGACTCTGAG ACTATCGAAC TCGCACCTGA ATACGCTGAG
    7060       7070       7080       7090       7100
GCTATCGCAA CCCGTGCAGG TGCGCTGGCT GGCATCTCTC CGATGTTCCA
    7110       7120       7130       7140       7150
ACCTTGCGTA GTTCCTCCTA AGCCGTGGAC TGGCATTACT GGTGGTGGCT
    7160       7170       7180       7190       7200
ATTGGGCTAA CGGTCGTCGT CCTCTGGCGC TGGTGCGTAC TCACAGTAAG
    7210       7220       7230       7240       7250
AAAGCACTGA TGCGCTACGA AGACGTTTAC ATGCCTGAGG TGTACAAAGC
    7260       7270       7280       7290       7300
GATTAACATT GCGCAAAACA CCGCATGGAA AATCAACAAG AAAGTCCTAG
    7310       7320       7330       7340       7350
CGGTCGCCAA CGTAATCACC AAGTGGAAGC ATTGTCCGGT CGAGGACATC
    7360       7370       7380       7390       7400
CCTGCGATTG AGCGTGAAGA ACTCCCGATG AAACCGGAAG ACATCGACAT
    7410       7420       7430       7440       7450
GAATCCTGAG GCTCTCACCG CGTGGAAACG TGCTGCCGCT GCTGTGTACC
    7460       7470       7480       7490       7500
GCAAGGACAA GGCTCGCAAG TCTCGCCGTA TCAGCCTTGA GTTCATGCTT
    7510       7520       7530       7540       7550
GAGCAAGCCA ATAAGTTTGC TAACCATAAG GCCATCTGGT TCCCTTACAA
    7560       7570       7580       7590       7600
CATGGACTGG CGCGGTCGTG TTTACGCTGT GTCAATGTTC AACCCGCAAG
    7610       7620       7630       7640       7650
```

FIG. 9-7

```
GTAACGATAT GACCAAAGGA CTGCTTACGC TGGCGAAAGG TAAACCAATC
    7660       7670       7680       7690       7700
GGTAAGGAAG GTTACTACTG GCTGAAAATC CACGGTGCAA ACTGTGCGGG
    7710       7720       7730       7740       7750
TGTCGATAAG GTTCCGTTCC CTGAGCGCAT CAAGTTCATT GAGGAAAACC
    7760       7770       7780       7790       7800
ACGAGAACAT CATGGCTTGC GCTAAGTCTC CACTGGAGAA CACTTGGTGG
    7810       7820       7830       7840       7850
GCTGAGCAAG ATTCTCCGTT CTGCTTCCTT GCGTTCTGCT TTGAGTACGC
    7860       7870       7880       7890       7900
TGGGGTACAG CACCACGGCC TGAGCTATAA CTGCTCCCTT CCGCTGGCGT
    7910       7920       7930       7940       7950
TTGACGGGTC TTGCTCTGGC ATCCAGCACT TCTCCGCGAT GCTCCGAGAT
    7960       7970       7980       7990       8000
GAGGTAGGTG GTCGCGCGGT TAACTTGCTT CCTAGTGAAA CCGTTCAGGA
    8010       8020       8030       8040       8050
CATCTACGGG ATTGTTGCTA AGAAAGTCAA CGAGATTCTA CAAGCAGACG
    8060       8070       8080       8090       8100
CAATCAATGG GACCGATAAC GAAGTAGTTA CCGTGACCGA TGAGAACACT
    8110       8120       8130       8140       8150
GGTGAAATCT CTGAGAAAGT CAAGCTGGGC ACTAAGGCAC TGGCTGGTCA
    8160       8170       8180       8190       8200
ATGGCTGGCT TACGGTGTTA CTCGCAGTGT GACTAAGCGT TCAGTCATGA
    8210       8220       8230       8240       8250
CGCTGGCTTA CGGGTCCAAA GAGTTCGGCT TCCGTCAACA AGTGCTGGAA
    8260       8270       8280       8290       8300
GATACCATTC AGCCAGCTAT TGATTCCGGC AAGGGTCTGA TGTTCACTCA
    8310       8320       8330       8340       8350
GCCGAATCAG GCTGCTGGAT ACATGGCTAA GCTGATTTGG GAATCTGTGA
    8360       8370       8380       8390       8400
GCGTGACGGT GGTAGCTGCG GTTGAAGCAA TGAACTGGCT TAAGTCTGCT
    8410       8420       8430       8440       8450
GCTAAGCTGC TGGCTGCTGA GGTCAAAGAT AAGAAGACTG GAGAGATTCT
    8460       8470       8480       8490       8500
TCGCAAGCGT TGCGCTGTGC ATTGGGTAAC TCCTGATGGT TTCCCTGTGT
    8510       8520       8530       8540       8550
GGCAGGAATA CAAGAAGCCT ATTCAGACGC GCTTGAACCT GATGTTCCTC
    8560       8570       8580       8590       8600
GGTCAGTTCC GCTTACAGCC TACCATTAAC ACCAACAAAG ATAGCGAGAT
    8610       8620       8630       8640       8650
TGATGCACAC AAACAGGAGT CTGGTATCGC TCCTAACTTT GTACACAGCC
    8660       8670       8680       8690       8700
AAGACGGTAG CCACCTTCGT AAGACTGTAG TGTGGGCACA CGAGAAGTAC
    8710       8720       8730       8740       8750
GGAATCGAAT CTTTTGCACT GATTCACGAC TCCTTCGGTA CCATTCCGGC
    8760       8770       8780       8790       8800
TGACGCTGCG AACCTGTTCA AAGCAGTGCG CGAAACTATG GTTGACACAT
    8810       8820       8830       8840       8850
ATGAGTCTTG TGATGTACTG GCTGATTTCT ACGACCAGTT CGCTGACCAG
    8860       8870       8880       8890       8900
TTGCACGAGT CTCAATTGGA CAAAATGCCA GCACTTCCGG CTAAAGGTAA
    8910       8920       8930       8940       8950
CTTGAACCTC CGTGACATCT TAGAGTCGGA CTTCGCGTTC GCGTAACGCC
    8960       8970       8980       8990       9000
```

FIG. 9-8

```
AAATCAATAC GACCCGGATC GGTCGACCTG CAGCCCAAGC TTGGCACTGG
    9010       9020       9030       9040       9050
CCGTCGTTTT ACAACGTCGT GACTGGGAAA ACCCTGGCGT TACCCAACTT
    9060       9070       9080       9090       9100
AATCGCCTTG CAGCACATCC CCCCTTCGCC AGCTGGCGTA ATAGCGAAGA
    9110       9120       9130       9140       9150
GGCCCGCACC GATCGCCCTT CCCAACAGTT GCGTAGCCTG AATGGCGAAT
    9160       9170       9180       9190       9200
GGCGCTTTGC CTGGTTTCCG GCACCAGAAG CGGTGCCGGA AAGCTGGCTG
    9210       9220       9230       9240       9250
GAGTGCGATC TTCCTGAGGC CGAQACNGTC GTCGTCCCCT CAAACTGGCA
    9260       9270       9280       9290       9300
GATGCACGGT TACGATGCGC CCATCTACAC CAACGTAACC TATCCCATTA
    9310       9320       9330       9340       9350
CGGTCAATCC GCCGTTTGTT CCCACGGAGA ATCCGACGGG TTGTTACTCG
    9360       9370       9380       9390       9400
CTCACATTTA ATGTTGATGA AAGCTGGCTA CAGGAAGGCC AGACGCGAAT
    9410       9420       9430       9440       9450
TATTTTTGAT GGCGTTCCTA TTGGTTAAAA AATGAGCTGA TTTAACAAAA
    9460       9470       9480       9490       9500
ATTTAACGCG AATTTTAACA AAATATTAAC GTTTACAATT TAAATATTTG
    9510       9520       9530       9540       9550
CTTATACAAT CTTCCTGTTT TTGGGGCTTT TCTGATTATC AACCGGGGTA
    9560       9570       9580       9590       9600
CATATGATTG ACATGCTAGT TTTACGATTA CCGTTCATCG ATTCTCTTGT
    9610       9620       9630       9640       9650
TTGCTCCAGA CTCTCAGGCA ATGACCTGAT AGCCTTTGTA GATCTCTCAA
    9660       9670       9680       9690       9700
AAATAGCTAC CCTCTCCGGC ATGAATTTAT CAGCTAGAAC GGTTGAATAT
    9710       9720       9730       9740       9750
CATATTGATG GTGATTTGAC TGTCTCCGGC CTTTCTCACC CTTTTGAATC
    9760       9770       9780       9790       9800
TTTACCTACA CATTACTCAG GCATTGCATT TAAAATATAT GAGGGTTCTA
    9810       9820       9830       9840       9850
AAAATTTTTA TCCTTGCGTT GAAATAAAGG CTTCTCCCGC AAAAGTATTA
    9860       9870       9880       9890       9900
CAGGGTCATA ATGTTTTTGG TACAACGAT  TTAGCTTTAT GCTCTGAGGC
    9910       9920       9930       9940       9950
TTTATTGCTT AATTTTGCTA ATTCTTTGCC TTGCCTGTAT GATTTATTGG

ATGTT
```

T7 DNA POLYMERASE

BACKGROUND OF THE INVENTION

This invention was made with government support including a grant from the U.S. Public Health Service, contract number AI-06045. The government has certain rights in the invention.

This is a continuation of co-pending application Ser. No. 003,227 filed on Jan. 14, 1987.

This invention relates to DNA polymerases suitable for DNA sequencing.

DNA sequencing involves the generation of four populations of single stranded DNA fragments having one defined terminus and one variable terminus. The variable terminus always terminates at a specific given nucleotide base (either guanine (G), adenine (A), thymine (T), or cytosine (C)). The four different sets of fragments are each separated on the basis of their length, on a high resolution polyacrylamide gel; each band on the gel corresponds colinearly to a specific nucleotide in the DNA sequence, thus identifying the positions in the sequence of the given nucleotide base.

Generally there are two methods of DNA sequencing. One method (Maxam and Gilbert sequencing) involves the chemical degradation of isolated DNA fragments, each labeled with a single radiolabel at its defined terminus, each reaction yielding a limited cleavage specifically at one or more of the four bases (G, A, T or C). The other method (dideoxy sequencing) involves the enzymatic synthesis of a DNA strand. Four separate syntheses are run, each reaction being caused to terminate at a specific base (G, A, T or C) via incorporation of the appropriate chain terminating dideoxynucleotide. The latter method is preferred since the DNA fragments are uniformly labelled (instead of end labelled) and thus the larger DNA fragments contain increasingly more radioactivity. Further, $^{35}$S-labelled nucleotides can be used in place of $^{32}$P-labelled nucleotides, resulting in sharper definition; and the reaction products are simple to interpret since each lane corresponds only to either G, A, T or C. The enzyme used for most dideoxy sequencing is the *Escherichia coli* DNA-polymerase I large fragment ("Klenow"). Another polymerase used is AMV reverse transcriptase.

SUMMARY OF THE INVENTION

In one aspect the invention features a method for determining the nucleotide base sequence of a DNA molecule, comprising annealing the DNA molecule with a primer molecule able to hybridize to the DNA molecule; incubating separate portions of the annealed mixture in at least four vessels with four different deoxynucleoside triphosphates, a processive DNA polymerase having less than 500 units of exonuclease activity per mg of polymerase, and a DNA synthesis terminating agent which terminates DNA synthesis at a specific nucleotide base. The agent terminates at a different specific nucleotide base in each of the four vessels. The DNA products of the incubating reaction are separated according to their size so that at least a part of the nucleotide base sequence of the DNA molecule can be determined.

In preferred embodiments the polymerase remains bound to the DNA molecule for at least 500 bases before dissociating, most preferably for at least 1,000 bases; the polymerase is substantially the same as one in cells infected with a T7-type phage (i.e., phage in which the DNA polymerase requires host thioredoxin as a subunit) for example, the T7-type phage is T7, T3, ΦI, ΦII, H, W31, gh-1, Y, A1122, or Sp6; the polymerase is non-discriminating for dideoxy nucleotide analogs; the polymerase is modified to have less than 50 units of exonuclease activity per mg of polymerase, more preferably less than 1 unit, even more preferably less than 0.1 unit, and most preferably has no detectable exonuclease activity; the polymerase is able to utilize primers of as short as 10 bases or preferably as short as 4 bases; the primer comprises four to forty nucleotide bases, and is single stranded DNA or RNA; the annealing step comprises heating the DNA molecule and the primer to above 65° C., preferably from 65° C. to 100° C., and allowing the heated mixture to cool to below 65° C., preferably to 10° C. to 30° C.; the incubating step comprises a pulse and a chase step, wherein the pulse step comprises mixing the annealed mixture with all four different deoxynucleoside triphosphates and a processive DNA polymerase, wherein at least one of the deoxynucleoside triphosphates is labelled; most preferably the pulse step performed under conditions in which the polymerase does not exhibit its processivity and is for 30 seconds to 20 minutes at 0° C. to 20° C. or where at least one of the nucleotide triphosphates is limiting; and the chase step comprises adding one of the chain terminating agents to four separate aliquots of the mixture after the pulse step; preferably the chase step is for 1 to 60 minutes at 30° C. to 50° C.; the terminating agent is a dideoxynucleotide, or a limiting level of one deoxynucleoside triphosphate; one of the four deoxynucleotides is chosen from dITP or deazaguanosine; and labelled primers are used so that no pulse step is required, preferably the label is radioactive fluorescent.

In other aspects the invention features (a) a method for producing blunt ended double-stranded DNA molecules from a linear DNA molecule having no 3' protruding termini, using a processive DNA polymerase free from exonuclease activity; (b) a method of amplification of a DNA sequence comprising annealing a first and second primer to opposite strands of a double stranded DNA sequence and incubating the annealed mixture with a processive DNA polymerase having less than 500 units of exonuclease activity per mg of polymerase, preferably less than 1 unit, wherein the first and second primers anneal to opposite strands of the DNA sequence; in preferred embodiments the primers have their 3' ends directed toward each other; and the method further comprises, after the incubation step, denaturing the resulting DNA, annealing the first and second primers to the resulting DNA and incubating the annealed mixture with the polymerase; preferably the cycle of denaturing, annealing and incubating is repeated from 10 to 40 times; (c) a method for in vitro mutagenesis of cloned DNA fragments, comprising providing a cloned fragment and synthesizing a DNA strand using a processive DNA polymerase having less than 1 unit of exonuclease activity per mg of polymerase; (d) a method of producing active T7-type DNA polymerase from cloned DNA fragments under the control of non-leaky promoters (see below) in the same cell comprising inducing expression of the genes only when the cells are in logarithmic growth phase, or stationary phase, and isolating the polymerase from the cell; preferably the cloned fragments are under the control of a promoter requiring T7 RNA polymerase for expression; (e) a gene encoding a T7-type DNA polymerase, the gene being genetically modified to reduce the activity of naturally occurring exonuclease activity; (f) the product of the gene encoding genetically modified polymerase; (g) a method of purifying T7 DNA polymerase from cells comPrising a vector from which the polymerase is expressed,, comprising the steps of lysing the cells, and passing the polymerase over a sizing column over a DE52 DEAE column, a phosphocellulose column, and a hydroxyapatite column; preferably prior to the passing step the method comprises precipitating the polymerase with ammonium sulfate; the method further comprises the step of passing the polymerase over a sephadex DEAE50 column; and the sizing column is a DE52 DEAE column; (h) a method of inactivating exonuclease activity in a DNA polymerase solution comprising incubating the solution in a vessel containing oxygen, a reducing agent and a transition metal; (i) a kit for DNA sequencing, comprising a processive DNA polymerase having less than 500 units of exonuclease activity per mg of polymerase, wherein the polymerase is able to exhibit it processivity in a first environmental condition, and unable to exhibit its processivity in a second environmental condition, and a reagent necessary for the sequencing, selected from a deoxynucleotide, a chain terminating agent, or an oligonucleotide primer; preferably the deoxynucleotide is dITP; (j) a method for labelling the 3' end of a DNA fragment comprising incubating the DNA fragment with a processive DNA polymerase having less than 500 units of exonuclease activity per mg of polymerase, and a labelled deoxynucleotide; (k) a method for in vitro mutagenesis of a cloned DNA fragment comprising providing a primer and a template, the primer and the template having a specific mismatched base, and extending the primer with a processive DNA polymerase; and (l) a method for in vitro mutagenesis of a cloned DNA fragment comprising providing the cloned fragment and synthesizing a DNA strand using a processive DNA polymerase, having less than 50 units of exonuclease activity, under conditions which cause misincorporation of a nucleotide base.

This invention provides a DNA polymerase which is processive, non-discriminating, and can utilize short primers. Further, the polymerase has no associated exonuclease activity. These are ideal properties for the above described methods, and in particular for DNA sequencing reactions, since the background level of radioactivity in the polyacylamide gels is negligible, there are few or no artifactual bands, and the bands are sharp—making the DNA sequence easy to read. Further, such a polymerase allows novel methods of sequencing long DNA fragments, as is described in detail below.

Other features and advantages of the invention will be apparent from the following description of the preferred embodiments thereof and from the claims.

DESCRIPTION OF THE PREFERRED EMBODIMENTS

The drawings will first briefly be described.

Drawings

FIG. 6 is a diagrammatic representation of the enzymatic amplification of genomic DNA using modified T7 DNA polymerase.

FIG. 7, 8 and 9 are the nucleotide sequences of pTrx-2, a part of pGP5-5 and mGP1-2 respectively.

DNA POLYMERASE

Figure 1:
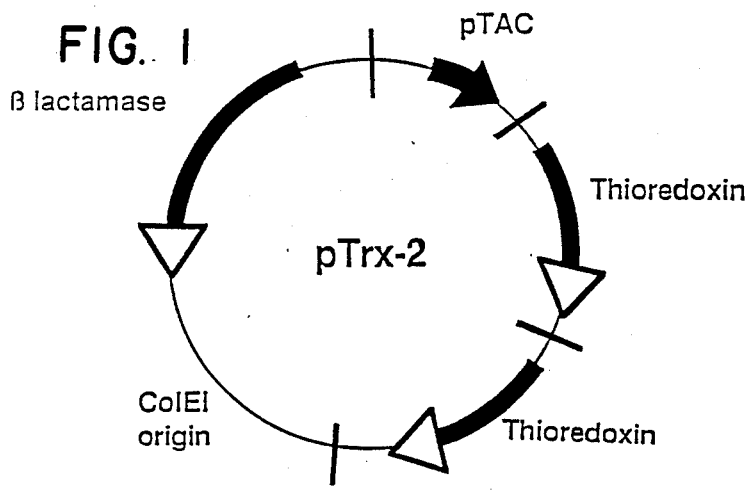
FIGS. 1-3 are diagrammatic representations of the vectors pTrx-2, mGP1-1, and pGP5-5 respectively.

In general the DNA polymerase of this invention is processive, has no associated exonuclease activity, does not discriminate against nucleotide analog incorPoration, and can utilize small oligonucleotides (such as tetramers, hexamers and octamers) as specific primers. These properties will now be discussed in detail.

Processivity

By processivity is meant that the DNA polymerase is able to continuously incorporate many nucleotides using the same primer-template without dissociating from the template. The degree of processivity varies with different polymerases: some incorporate only a few bases before dissociating (e.g. Klenow, T4 DNA polymerase, and reverse transcriptase) while others, such as those of the present invention, will remain bound for at least 500 bases and preferably at least 1,000 bases under suitable environmental conditions. Such environmental conditions include having adequate supplies of all four deoxynucleoside triphosphates and an incubation temperature from 10° C.–50° C. Processivity is greatly enhanced in the presence of $E.\ coli$ single stranded binding (ssb), protein.

With processive enzymes termination of a sequencing reaction will occur only at those bases which have incorporated a chain terminating agent, such as a dideoxynucleotide. If the DNA polymerase is non-processive, then artifactual bands will arise during sequencing reactions, at positions corresponding to the nucleotide where the polymerase dissociated. Frequent dissociation creates a background of bands at incorrect positions and obscures the true DNA sequence. This problem is partially corrected by incubating the reaction mixture for a long time (30–60 min) with a high concentration of substrates, which "chase" the artifactual bands up to a high molecular weight at the top of the gel, away from the region where the DNA sequence is read. This is not an ideal solution since a non-processive DNA polymerase has a high probability of dissociating from the template at regions of compact secondary structure, or hairpins. Reinitiation of primer elongation at these sites is inefficient and the usual result is the formation of bands at the same position for all four nucleotides, thus obscuring the DNA sequence.

Analog discrimation

The DNA polymerases of this invention do not discriminate significantly between dideoxy-nucleotide analogs and normal nucleotides. That is, the chance of incorporation of an analog is approximately the same as that of a normal nucleotide. The polymerases of this invention also do not discriminate significantly against some other analogs. This is important since, in addition to the four normal deoxynucleoside triphosphates (dGTP, dATP, dTTP and dCTP), sequencing reactions require the incorporation of other types of nucleotide derivatives such as: radioactively- or fluorescently-labelled nucleoside triphosphates, usually for labeling the synthesized strands with $^{35}S$, $^{32}P$, or other chemical agents. When a DNA polymerase does not discriminate against analogs the same probability will exist for the incorporation of an analog as for a normal nucleotide. For labelled nucleoside triphosphates this is important in order to efficiently label the synthesized DNA strands using a minimum of radioactivity. Further, lower levels of analogs are required with such enzymes, making the sequencing reaction cheaper than with a discriminating enzyme.

Discriminating polymerases show a different extent of discrimination when they are polymerizing in a processive mode versus when stalled, struggling to synthesize through a secondary structure impediment. At such impediments there will be a variability in the intensity of different radioactive bands on the gel, which may obscure the sequence.

Exonuclease Activity

The DNA polymerase of the invention has less than 50%, preferably less than 1%, and most preferably less than 0.1%, of the normal or naturally associated level of exonuclease activity (amount of activity per polymerase molecule). By normal or naturally associated level is meant the exonuclease activity of unmodified T7-type polymerase. Normally the associated activity is about 5,000 units of exonuclease activity per mg of polymerase, measured as described below by a modification of the procedure of Chase et al. (249 J. Biol. Chem. 4545, 1974). Exonucleases increase the fidelity of DNA synthesis by excising any newly synthesized bases which are incorrectly basepaired to the template. Such associated exonuclease activities are detrimental to the quality of DNA sequencing reactions. They raise the minimal required concentration of nucleotide Precursors which must be added to the reaction since, when the nucleotide concentration falls, the polymerase activity slows to a rate comparable with the exonuclease activity, resulting in no net DNA synthesis, or even degradation of the synthesized DNA.

More importantly, associated exonuclease activity will cause a DNA polymerase to idle at regions in the template with secondary structure impediments. When a polymerase approaches such a structure its rate of synthesis decreases as it struggles to pass. An associated exonuclease will excise the newly synthesized DNA when the polymerase stalls. As a consequence numerous cycles of synthesis and excision will occur. This may result in the polymerase eventually synthesizing past the hairpin (with no detriment to the quality of the sequencing reaction); or the polymerase may dissociate from the synthesized strand (resulting in an artifactual band at the same position in all four sequencing reactions); or, a chain terminating agent may be incorporated at a high frequency and produce a wide variability in the intensity of different fragments in a sequencing gel. This happens because the frequency of incorporation of a chain terminating agent at any given site increases with the number of opportunities the polymerase has to incorporate the chain terminating nucleotide, and so the DNA polymerase will incorporate a chain-terminating agent at a much higher frequency at sites of idling than at other sites.

An ideal sequencing reaction will produce bands of uniform intensity throughout the gel. This is essential for obtaining the optimal exposure of the X-ray film for every radioactive fragment. If there is variable intensity of radioactive bands, then fainter bands have a chance of going undetected. To obtain uniform radioactive intensity of all fragments, the DNA polymerase should spend the same interval of time at each position on the DNA, showing no preference for either the additon or removal of nucleotides at any given site. This occurs if the DNA polymerase lacks any associated exonuclease, so that it will have only one opportunity to incorporate a chain terminating nucleotide at each position along the template.

Short primers

The DNA polymerase of the invention is able to utilize primers of 10 bases or less, as well as longer ones, most preferably of 4–20 bases. The ability to utilize short primers offers a number of important advantages to DNA sequencing. The shorter primers are cheaper to buy and easier to synthesize than the usual 15–20-mer primers. They also anneal faster to complementary sites on a DNA template, thus making the sequencing reaction faster. Further, the ability to utilize small (e.g., six or seven base) oligonucleotide primers for DNA sequencing permits strategies not otherwise possible for sequencing long DNA fragments. For example, a kit containing 80 random hexamers could be generated, none of which are complementary to any sites in the cloning vector. Statistically, one of the 80 hexamer sequences will occur an average of every 50 bases along the DNA fragment to be sequenced. The determination of a sequence of 3000 bases would require only five sequencing cycles. First, a "universal" primer (e.g., Biolabs #1211, sequence 5' GTAAAACGACGG-CCAGT 3') would be used to sequence about 600 bases at one end of the insert. Using the results from this sequencing reaction, a new primer would be picked from the kit homologous to a region near the end of the determined sequence. In the second cycle, the sequence of the next 600 bases would be determined using this primer. Repetition of this process five times would determine the complete sequence of the 3000 bases, without necessitating any subcloning, and without the chemical synthesis of any new oligonucleotide primers. The use of such short primers is enhanced by including gene 2.5 and 4 protein of T7 in the sequencing reaction.

DNA polymerases of this invention, (i.e., having the above properties) include modified T7-type polymerases. That is the DNA polymerase requires host thioredoxin as a sub-unit, and they are substantially identical to a modified T7 DNA polymerase or to equivalent enzymes isolated from related phage, such as T3, ΦI, ΦII, H, W31, gh-1, Y, A1122 and Sp6. Each of these enzymes can be modified to have properties similar to those of the modified T7 enzyme. It is possible to isolate the enzyme from phage infected cells directly, but preferably the enzyme is isolated from cells which overproduce it. By substantially identical is meant that the enzyme may have amino acid substitutions which do not affect the overall properties of the enzyme. One example of a particularly desirable amino acid substitution is one in which the natural enzyme is modified to remove any exonuclease activity. This modification may be performed at the genetic or chemical level (see below).

Cloning T7 polymerase

As an example of the invention we shall describe the cloning, overproduction, purification, modification and use of T7 DNA polymerase. This enzyme consists of two polypeptides tightly complexed in a one to one stoichiometry. One is the phage T7-encoded gene 5 protein of 84,000 daltons (Modrich et al. 150 J. Biol. Chem. 5515, 1975), the other is the *E. coli* encoded thioredoxin, of 12,000 daltons (Tabor et al., 82 Proc. Natl. Acad. Sci. 1074, 1985). The thioredoxin is an accessory protein and attaches the gene 5 protein (the actual DNA polymerase) to the primer template. The natural DNA polymerase has a very active 3' to 5' exonuclease associated with it. This activity makes the polymerase useless for DNA sequencing and must be inactivated or modified before the polymerase can be used. This is readily performed, as described below, either chemically, by local oxidation of the exonuclease domain, or genetically, by modifying the coding region of the polymerase gene encoding this activity.

pTrx-2

In order to clone the trxA (thioredoxin) gene of *E. coli* wild type *E. coli* DNA was partially cleaved with Sau3A and the fragments ligated to BamHI-cleaved T7 DNA isolated from strain T7 ST9 (Tabor et al., in Thioredoxin and Glutaredoxin Systems: Sturcture and Function (Holmgren et al., eds) pp. 285–300, Raven Press, N.Y.; and Tabor et al., supra). The ligated DNA was transfected into *E. coli* trxA⁻ cells, the mixture plated onto trxA⁻ cells, and the resulting T7 plaques picked. Since T7 cannot grow without an active *E. coli* trxA gene only those phages containing the trxA gene could form plaques. The cloned trxA genes were located on a 470 base pair HincII fragment.

Figure 2:
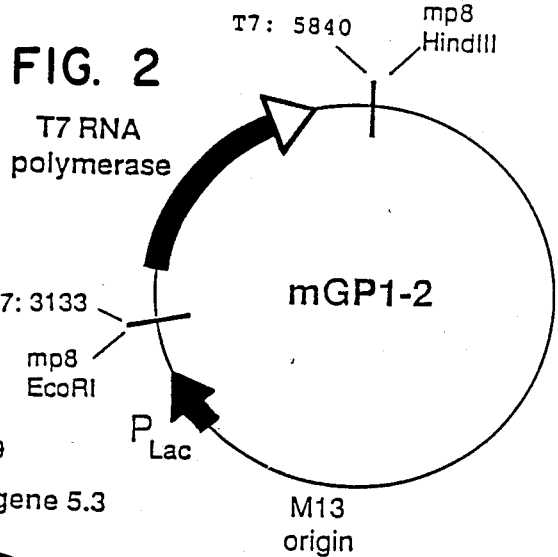

In order to overproduce thioredoxin a plasmid, pTrx-2, was as constructed. Briefly, the 470 base pair HincII fragment containing the trxA gene was isolated by standard procedure (Maniatis et al., Cloning: A Laboratory Manual, Cold Spring Harbor Labs., Cold Spring Harbor, N.Y.), and ligated to a derivative of pBR322 containing a Ptac promoter (ptac-12, Amann et al., 25 Gene 167, 1983). Referring to FIG. 2, ptac-12, containing β-lactamase and Col El origin, was cut with PvuII, to yield a fragment of 2290 bp, which was then ligated to two tandem copies of trxA (HincII fragment) using commercially available linkers (SmaI-BamHI polylinker), to form pTrx-2. The complete nucleotide sequence of pTrx-2 is shown in FIG. 7. Thioredoxin production is now under the control of the tac promoter, and thus can be specifically induced, e.g. by IPTG (isopropyl β-D-thiogalactoside).

pGP5-5 and mGP1-2

Some gene products of T7 are lethal when expressed in *E. coli*. An expression system was developed to facilitate cloning and expression of, lethal genes, based on the inducible expression of T7 RNA polymerase. Gene 5 protein is lethal in some *E. coli* strains and an example of such a system is described by Tabor et al. 82 Proc. Nat. Acad. Sci. 1074 (1985) where T7 gene 5 was placed under the control of the Φ10 promoter, and is only expressed when T7 RNA polymerase is present in the cell.

Briefly, pGP5-5 (FIG. 3) was constructed by standard procedures using synthetic BamHI linkers to join T7 fragment from 14306 (NdeI) to 16869 (AhaIII), containing gene 5, to the 560 bp fragment of T7 from 5667 (HincII) to 6166 (Fnu4HI) containing both the Φ1.1A and Φ1.1B promoters, which are recognized by T7 RNA polymerase, and the 3kb BamHI-HincII fragment of pACYC177 (Chang et al., 134 J. Bacteriol. 1141, 1978). The nucleotide sequence of the T7 inserts and linkers in shown in FIG. 8. In this plasmid gene 5 is only expressed when T7 RNA polymerase is provided in the cell.

Figure 3:
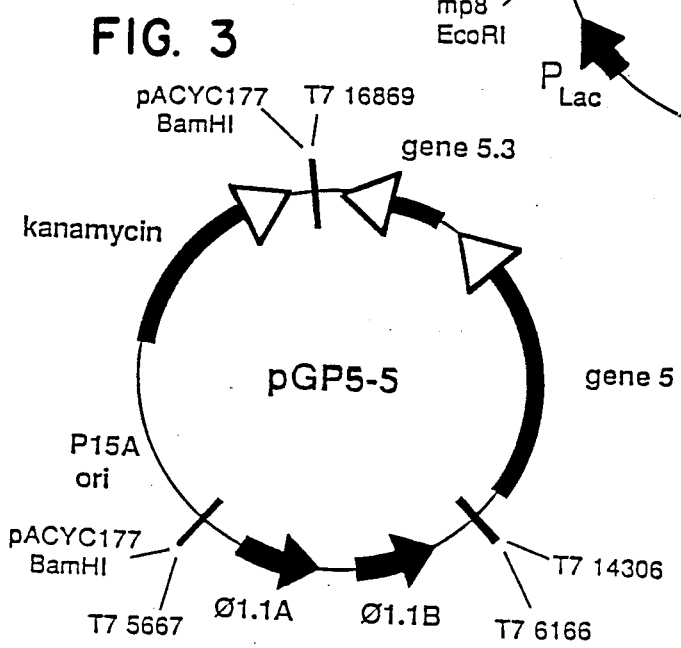

Referring to FIG. 3, T7 RNA polymerase is provided on phage vector mGP1-2. This is similar to pGP1-2 (Tabor et al., id.) except that the fragment of T7 from 3133 (HaeIII) to 5840 (HinfI), containing T7 RNA polymerase was ligated, using linkers (BglII and SalI respectively), to BamHI-SalI cut M13 mp8, placing the polymerase gene under control of the lac promoter. The complete nucleotide sequence of mGP1-2 is shown in FIG. 9.

Since pGP5-5 and pTrx-2 have different origins of replication (respectively a P15A and a ColEl origin) they can be tranformed into one cell simultaneously. pTrx-2 expresses large quantities of thioredoxin in the presence of IPTG. mGP1-2 can coexist in the same cell as these two plasmids and be used to regulate expression of T7-DNA polymerase from pGP5-5, simply by causing production of T7-RNA polymerase by inducing the lac promoter with, e.g., IPTG.

Overproduction of T7 DNA polymerase

There are several potential strategies for overproducing and reconstituting the two gene products of trxA and gene 5. The same cell strains and plasmids can be utilized for all the strategies. In the preferred strategy the two genes are co-overexpressed in the same cell. (This is because gene 5 is susceptible to proteases until thioredoxin is bound to it.) As described in detail below, one procedure is to place the two genes separately on each of two compatible plasmids in the same cell. Alternatively, the two genes could be placed in tandem on the same plasmid. It is important that the T7-gene 5 is placed under the control of a non-leaky inducible promoter, such as Φ1.1A, Φ1.1B and Φ10 of T7, as the synthesis of even small quantities of the two polypeptides together is toxic in most *E. coli* cells. By non-leaky is meant that less than 500 molecules of the gene product are produced, per cell generation time, from the gene when the promoter, controlling the gene's expression, is not activated. Preferably the T7 RNA polymerase expression system is used although other expression systems which utilize inducible promoters could also be used. A leaky promoter, e.g., plac, allows more than 500 molecules of protein to be synthesized, even when not induced, thus cells containing lethal genes under the control of such a promoter grow poorly and are not suitable in this invention. It is of course possible to produce these products in cells where they are not lethal, for example, the plac promoter is suitable in such cells.

In a second strategy each gene can be cloned and overexpressed separately. Using this strategy, the cells containing the individually overproduced polypeptides are combined prior to preparing the extracts, at which point the two polypeptides form an active T7 DNA polymerase.

EXAMPLE 1: PRODUCTION OF T7 DNA POLYMERASE

*E. coli* strain JM103 (Messing et al., 9 Nuc. Acid Res. 309, 1981) is used for preparing stocks of mGP1-2. JM103 is stored in 50% glycerol at −80° C. and is streaked on a standard minimal media agar plate. A single colony is grown overnight in 25 ml standard M9 media at 37° C., and a single plaque of mGP1-2 is obtained by titering the stock using freshly prepared JM103 cells. The plaque is used to inoculate 10 ml 2×LB (2% Bacto-Tryptone, 1% yeast extract, 0.5% NaCl, 8mM NaOH) containing JM103 grown to an $A_{590}=0.5$. This culture will provide the phage stock for preparing a large culture of mGP1-2. After 3-12 hours, the 10 ml culture is centrifuged, and the supernatant used to infect the large (2L) culture. For the large culture, 4×500 ml 2×LB is inoculated with 4×5 ml 71.18 cells grown in M9, and is shaken at 37° C. When the large culture of cells has grown to an $A_{590}=1.0$ (approximately three hours), they are inoculated with 10 ml of supernatant containing the starter lysate of mGP1-2. The infected cells are then grown overnight at 37° C. The next day, the cells are removed by centrifugation, and the supernatant is ready to use for induction of K38/pGP5-5/pTrx-2 (see below). The supernatant can be stored at 4° C. for approximately six months, at a titer ~$5 \times 10^{11}$ Φ/ml. At this titer, 1 L of phage will infect 12 liters of cells at an $A_{590}=5$ with a multiplicity of infection of 15. If the titer is low, the mGP1-2 phage can be concentrated from the supernatant by dissolving NaCl (60 gm/liter) and PEG-6000 (65 gm/liter) in the supernatant, allowing the mixture to settle at 0° C. for 1-72 hours, and then centrifuging (7000 rpm for 20 min). The precipitate, which contains the mGP1-2 phage, is resuspended in approximately 1/20th of the original volume of M9 media.

K38/pGP5-5/pTrx-2 is the *E. coli* strain (genotype HfrC (λ)) containing the two compatible plasmids pGP5-5 and pTrx-2. pGP5-5 plasmid has a P15A origin of replication and expresses the kanamycin (Km) resistance gene. pTrx-2 has a ColEI origin of replication and expresses the ampicillin (Ap) resistance gene. The plasmids are introduced into K38 by standard procedures, selecting $Km^R$ and $Ap^R$ respectively. The cells K38/pGP5-5/pTrx-2 are stored in 50% glycerol at −80° C. Prior to use they are streaked on a plate containing 50 μg/ml ampicillin and kanamycin, grown at 37° C. overnight, and a single colony grown in 10 ml LB media containing 50 μg/ml ampicillin and kanamycin, at 37° C. for 4-6 hours. The 10 ml cell culture is used to inoculate 500 ml of LB media containing 50 μg/ml ampicillin and kanamycin and shaken at 37° C. overnight. The following day, the 500 ml culture is used to inoculate 12 liters of 2× LB-KPO₄ media (2% Bacto-Tryptone, 1% yeast extract, 0.5% NaCl, 20 mM KPO₄, 0.2% dextrose, and 0.2% casamino acids, pH 7.4), and grown with aeration in a fermentor at 37° C. When the cells reach an $A_{590}=5.0$ (i.e. logarithmic or stationary phase cells), they are infected with mGP1-2 at a multiplicity of infection of 10, and IPTG is added (final concentration 0.5mM). The IPTG induces production of thioredoxin and the T7 RNA polymerase in mGP1-2, and thence induces production of the cloned DNA polymerase. The cells are grown for an additional 2.5 hours with stirring and aeration, and then harvested. The cell pellet is resuspended in 1.5 L 10% sucrose/20 mM Tris-HCl, pH 8.0/25 mM EDTA and re-spun. Finally, the cell pellet is resuspended in 200 ml 10% sucrose/20 mM Tris-HCl, pH 8/1.0 mM EDTA, and frozen in liquid N₂. From 12 liters of induced cells 70 gm of cell paste are obtained containing approximately 700 mg gene 5 protein and 100 mg thioredoxin.

K38/pTrx-2 (K38 containing pTrx-2 alone) overproduces thioredoxin, and it is added as a "booster" to extracts of K38/pGP5-5/pTrx-2 to insure that thioredoxin is in excess over gene 5 protein at the outset of the purification. The K38/pTrx-2 cells are stored in 50% glycerol at −80° C. Prior to use they are streaked on a plate containing 50 μg/ml ampicillin, grown at 37° C. for 24 hours, and a single colony grown at 37° C. overnight in 25 ml LB media containing 50 μg/ml ampicillin. The 25 ml culture is used to inoculate 2 L of 2× LB media and shaken at 37° C. When the cells reach an $A_{590}=3.0$, the ptac promoter, and thus thioredoxin production, is induced by the addition of IPTG (final concentration 0.5 mM). The cells are grown with shaking for an additional 12-16 hours at 37° C., harvested, resuspended in 600 ml 10% sucrose/20 mM Tris-HCl, pH 8.0/25 mM EDTA, and re-spun. Finally, the cells are resuspended in 40 ml 10% sucrose/20 mM Tris-HCl, pH 8/0.5 mM EDTA, and frozen in liquid N₂. From 2L of cells 16 gm of cell paste are obtained containing 150 mg of thioredoxin.

Assays for the polymerase involve the use of single-stranded calf thymus DNA (6mM) as a substrate. This is prepared immediately prior to use by denaturation of double-stranded calf thymus DNA with 50 mM NaOH at 20° C. for 15 min., followed by neutralization with HCl. Any purified DNA can be used as a template for the polymerase assay, although preferably it will have a length greater than 1,000 bases.

The standard T7 DNA polymerase assay used is a modification of the procedure described by Grippo et al. (246 J. Biol. Chem. 6867, 1971). The standard reaction mix (200 μl final volume) contains 40 mM Tris/HCl pH 7.5, 10 mM MgCl₂, 5 mM dithiothreitol, 100 nmol alkali-denatured calf thymus DNA, 0.3 mM dGTP, dATP, dCTP and [³H]dTTP (20 cpm/pm), 50 μg/ml BSA, and varying amounts of T7 DNA polymerase. Incubation is at 37° C. (10° C.-45° C.) for 30 min (5 min-60 min). The reaction is stopped by the addition of 3 ml of cold (0° C.) 1 N HCl-0.1 M pyrophosphate. Acid-insoluble radioactivity is determined by the procedure of Hinkle et al. (250 J. Biol. Chem. 5523, 1974). The DNA is precipitated on ice for 15 min (5 min-12 hr), then precipitated onto glass-fiber filters by filtration. The filters are washed five times with 4 ml of cold (0° C.) 0.1M HCl-0.1M pyrophosphate, and twice with cold (0° C.) 90% ethanol. After drying, the radioactivity on the filters is counted using a non-aqueous scintillation fluor.

One unit of polymerase activity catalyzes the incorporation of 10 nmol of total nucleotide into an acid-soluble form in 30 min at 37° C., under the conditions given above. Native T7 DNA polymerase and modified T7 DNA polymerase (see below) have the same specific polymerase activity ±20%, which ranges between 5,000-8,000 units/mg depending upon the preparation, using the standard assay conditions stated above.

T7 DNA polymerase is purified from the above extracts by precipitation and chromatography techniques. An example of such a purification follows.

An extract of frozen cells (200 ml K38/pGP5-5/pTrx-2 and 40 ml K38/pTrx-2) are thawed at 0° C. overnight. The cells are combined, and 5 ml of lysozyme (15 mg/ml) and 10 ml of NaCl (5M) are added. After 45 min at 0° C., the cells are placed in a 37° C. water bath until their temperature reaches 20° C. The cells are then frozen in liquid N₂. An additional 50 ml of NaCl (5M) is added, and the cells are thawed in a 37° C. water bath. After thawing, the cells are gently mixed at 0° C. for 60 min. The lysate is centrifuged for one hr at 35,000 rpm in a Beckman 45Ti rotor. The supernatant (250 ml) is fraction I. It contains approximately 700 mg gene 5 protein and 250 mg of thioredoxin (a 2:1 ratio thioredoxin to gene 5 protein).

90 gm of ammonium sulphate is dissolved in fraction I (250 ml) and stirred for 60 min. The suspension is allowed to sit for 60 min, and the resulting precipitate collected by centrifugation at 8000 rpm for 60 min. The precipitate is redissolved in 300 ml of 20 mM Tris-HCl pH 7.5/5 mM 2-mercaptoethanol/0.1 mM EDTA/10% glycerol (Buffer A). This is fraction II.

A column of Whatman DE52 DEAE (12.6 $cm^2 \times 18$ cm) is prepared and washed with Buffer A. Fraction II is dialyzed overnight against two changes of 1 L of Buffer A each (the buffer having a final conductivity equal to that of Buffer A containing 100 mM NaCl). Dialyzed Fraction II is applied to the column at a flow rate of 100 ml/hr, and washed with 400 ml of Buffer A containing 100 mM NaCl. Proteins are eluted with a 3.5 L gradient from 100 to 400 mM NaCl in Buffer A at a flow rate of 60 ml/hr. Fractions containing T7 DNA polymerase, which elutes at 200 mM NaCl, are pooled. This is fraction III (190 ml).

A column of Whatman P11 phosphocellulose (12.6 $cm^2 \times 12$ cm) is prepared and washed with 20 mM $KPO_4$ pH 7.4/5 mM 2-mercaptoethanol/0.1 mM EDTA/10 % glycerol (Buffer B). Fraction III is diluted 2-fold (380 ml) with Buffer B, then applied to the column at a flow rate of 60 ml/hr, and washed with 200 ml of Buffer B containing 100mM KCl. Proteins are eluted with a 1.8 L gradient from 100 to 400 mM KCl in Buffer B at a flow rate of 60 ml/hr. Fractions containing T7 DNA polymerase, which elutes at 300 mM KCl, are pooled. This is fraction IV (370 ml).

A column of DEAE-Sephadex A-50 (4.9 $cm^2 \times 15$ cm) is prepared and washed with 20 mM Tris-HCl 7.0/0.1 mM dithiothreitol/0.1 mM EDTA/10% glycerol (Buffer C). Fraction IV is dialyzed against two changes of 1 L Buffer C to a final conductivity equal to that of Buffer C containing 100 mM NaCl. Dialyzed fraction IV is applied to the column at a flow rate of 40 ml/hr, and washed with 150 ml of Buffer C containing 100 mM NaCl. Proteins are eluted with a 1 L gradient from 100 to 300 mM NaCl in Buffer C at a flow rate of 40 ml/hr. Fractions containing T7 DNA polymerase, which elutes at 210 mM NaCl, are pooled. This is fraction V (120 ml).

A column of BioRad HTP hydroxylapatite (4.9 $cm^2 \times 15$ cm) is prepared and washed with 20 mM $KPO_4$, pH 7.4/10 mM 2-mercaptoethanol/2 mM Na citrate/10% glycerol (Buffer D). Fraction V is dialyzed against two changes of 500 ml Buffer D each. Dialyzed fraction V is applied to the column at a flow rate of 30 ml/hr, and washed with 100 ml of Buffer D. Proteins are eluted with a 900 ml gradient from 0 to 180 mM $KPO_4$, pH 7.4 in Buffer D at a flow rate of 30 ml/hr. Fractions containing T7 DNA polymerase, which elutes at 50 mM $KPO_4$, are pooled. This is fraction VI (130 ml). It contains 270 mg of homogeneous T7 DNA polymerase.

Fraction VI is dialyzed versus 20 mM $KPO_4$ pH 7.4/0.1 mM dithiothreitol/0.1 mM EDTA/50% glycerol. This is concentrated fraction VI (~65 ml, 4 mg/ml), and is stored at $-20°$ C.

The isolated T7 polymerase has exonuclease activity associated with it. As stated above this must be inactivated. An example of inactivation by chemical modification follows.

Concentrated fraction VI is dialyzed overnight against 20 mM $KPO_4$ pH 7.4/0.1 mM dithiothreitol/10% glycerol to remove the EDTA present in the storage buffer. After dialysis, the concentration is adjusted to 2 mg/ml with 20 mM $KPO_4$ pH 7.4/0.1 mM dithiothreitol/10% glycerol, and 30 ml (2mg/ml) aliquots are placed in 50 ml polypropylene tubes. (At 2 mg/ml, the molar concentration of T7 DNA polymerase is 22 $\mu M$.)

Dithiothreitol (DTT) and ferrous ammonium sulfate $(Fe(NH_4)_2(SO_4)_2 6H_2O)$ are prepared fresh immediately before use, and added to a 30 ml aliquot of T7 DNA polymerase, to concentrations of 5 mM DTT (0.6 ml of a 250 mM stock) and 20 $\mu M$ $Fe(NH_4)_2(SO_4)_2 6H_2O$ (0.6 ml of a 1 mM stock). During modification the molar concentrations of T7 DNA polymerase and iron are each approximately 20 $\mu M$, while DTT is in 250× molar excess.

The modification is carried out at 0° C. under a saturated oxygen atmosphere as follows. The reaction mixture is placed on ice within a dessicator, the dessicator is purged of air by evacuation and subsequently filled with 100% oxygen. This cycle is repeated three times. The reaction can be performed in air (20% oxygen), but occurs at one third the rate.

Figure 4:
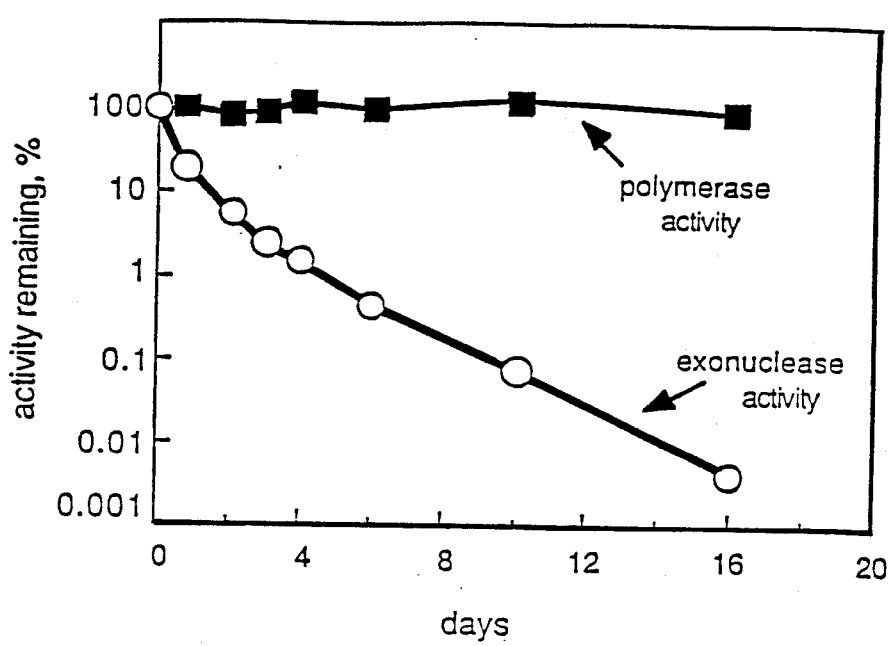
FIG. 4 is a graphical representation of the selective oxidation of T7 DNA polymerase.
Figure 5:
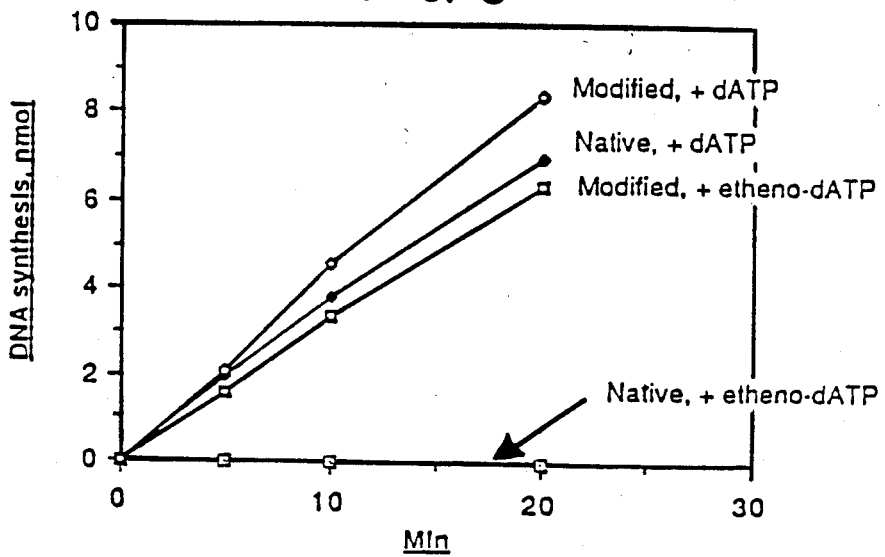
FIG. 5 is a graphical representation of the ability of modified T7 polymerase to synthesize DNA in the presence of etheno-dATP.

The time course of loss of exonuclease activity is shown in FIG. 4. $^3$H-labeled double-stranded DNA (6 cpm/pmol) was prepared from bacteriophage T7 as described by Richardson (15 J. Molec. Biol. 49, 1966). $^3$H-labeled single-stranded T7 DNA was prepared immediately prior to use by denaturation of double-stranded $^3$H-labeled T7 DNA with 50 mM NaOH at 20° C. for 15 min, followed by neutralization with HCl. The standard exonuclease assay used is a modification of the procedure described by Chase et al. (supra). The standard reaction mix (100 $\mu l$ final volume) contained 40 mM Tris/HCl pH 7.5, 10 mM $MgCl_2$, 10 mM dithiothreitol, 60 nmol $^3$H-labeled single-stranded T7 DNA (6 cpm/pm), and varying amounts of T7 DNA polymerase. $^3$H-labeled double-stranded Ty DNA can also be used as a substrate. Also, any uniformly radioactively labeled DNA, single- or double-stranded, can be used for the assay. Also, 3' end labeled single- or double-stranded DNA can be used for the assay. After incubation at 37° C. for 15 min, the reaction is stopped by the addition of 30 $\mu l$ of BSA (10mg/ml) and 25 $\mu l$ of TCA (100% w/v). The assay can be run at 10° C.–45° C. for 1–60 min. The DNA is precipitated on ice for 15 min (1 min–12 hr), then centrifuged at 12,000 g for 30 min (5 min–3 hr). 100 $\mu l$ of the supernatant is used to determine the acid-soluble radioactivity by adding it to 400 $\mu l$ water and 5 ml of aqueous scintillation cocktail.

One unit of exonuclease activity catalyzes the acid solubilization of 10 nmol of total nucleotide in 30 min under the conditions of the assay. Native T7 DNA polymerase has a specific exonuclease activity of 5000 units/mg, using the standard assay conditions stated above. The specific exonulease activity of the modified T7 DNA polymerase depends upon the extent of chemical modification, but ideally is at least 10-100-fold lower than that of native T7 DNA polymerase, or 500 to 50 or less units/mg using the standard assay conditions stated above.

Under the conditions outlined, the exonuclease activity decays exponentially, with a half-life of decay of eight hours. Once per day the reaction vessel is mixed to distribute the soluble oxygen, otherwise the reaction will proceed more rapidly at the surface where the concentration of oxygen is higher. Once per day 2.5 mM DTT (0.3 ml of a fresh 250 mM stock to a 30 ml reaction) is added to replenish the oxidized DTT.

After eight hours, the exonuclease activity of T7 DNA polymerase has been reduced 50%, with negligable loss of polymerase activity. The 50% loss is the result of the complete inactivation of exonuclease activity of half the polymerase molecules, rather than a general reduction of the rate of exonuclease activity in all the molecules. Thus, after an eight hour reaction all the molecules have normal polymerase activity, half the molecules have normal exonuclease activity, while the other half have <0.01% of their original exonuclease activity.

When 50% of the molecules are modified (an eight hour reaction), the enzyme is suitable, although suboptimal, for DNA sequencing. For more optimum quality of DNA sequencing, the reaction is allowed to proceed to greater than 99% modification (having less than 50 units of exonuclease activity), which requires four days.

After four days, the reaction mixture is dialyzed against 2 changes of 250 ml of 20 mM $KPO_4$ pH 7.4/0.1 mM dithiothreitol/0.1 mM EDTA/50% glycerol to remove the iron. The modified T7 DNA polymerase (~4 mg/ml) is stored at −20° C.

The reaction mechanism for chemical modification of T7 DNA polymerase depends upon reactive oxygen species generated by the presence of reduced transition metals such as $Fe^{2+}$ and oxygen. A possible reaction mechanism for the generation of hydroxyl radicals is outlined below:

(1) $Fe^{2+} + O_2 \rightarrow Fe^{3+} + O_2\cdot$
(2) $2O_2\cdot + 2H^+ \rightarrow H_2O_2 + O_2$
(3) $Fe^{2+} + H_2O_2 \rightarrow Fe^{3+} + OH\cdot + OH\cdot$ In equation 1, oxidation of the reduced metal ion yields superoxide radical, $O_2\cdot$. The superoxide radical can undergo a dismutation reaction, producing hydrogen peroxide (equation 2). Finally, hydrogen peroxide can react with reduced metal ions to form hydroxyl radicals, $OH\cdot$ (the Fenton reaction, equation 3). The oxidized metal ion is recycled to the reduced form by reducing agents such as dithiothreitol (DTT).

These reactive oxygen species probably inactivate proteins by irreversibly chemically altering specific amino acid residues. Such damage is observed in SDS-PAGE of fragments of gene 5 produced by CNBr or trypsin. Some fragments disappear, high molecular weight cross linking occurs, and some fragments are broken into two smaller fragments.

As previously mentioned, oxygen, a reducing agent (e.g. DTT, 2-mercaptoethanol) and a transition metal (e.g. iron) are essential elements of the modification reaction. The reaction occurs in air, but is stimulated three-fold by use of 100% oxygen. The reaction will occur slowly in the absence of added transition metals due to the presence of trace quantities of transition metals (1-2 $\mu$M) in most buffer preparations.

As expected, inhibitors of the modification reaction include anaeorobic conditions (e.g., $N_2$) and metal chelators (e.g. EDTA, citrate,, nitrilotriacetate). In addition, the enzymes catalase and superoxide dismutase inhibit the reaction, consistent with the essential role of reactive oxygen species in the generation of modified T7 DNA polymerase.

As an alternative procedure, it is possible to genetically mutate the T7 gene 5 to specifically inactivate the exonuclease domain of the protein. The T7 gene 5 protein purified from such mutants is ideal for use in DNA sequencing without the need to chemically inactivate the exonuclease by oxidation.

Genetically modified T7 DNA polymerase is isolated by randomly mutagenizing the gene 5 and then screening for those mutants that have lost exonuclease activity, without loss of polymerase activity. Mutagenesis is performed as follows. Single-stranded DNA containing gene 5 (e.g., cloned in pEMBL-8, a plasmid containing an origin for single stranded DNA replication) is prepared by standard procedure, and treated with two different chemical mutagens: hydrazine, which will mutate C's and T's, and formic acid, which will mutate G's and A's. Myers et al. 229 Science 242, 1985. The DNA is mutagenized at a dose which results in an average of one base being altered per plasmid molecule. The single-stranded mutagenized plasmids are then primed with a universal 17-mer primer (see above), and used as templates to synthesize the opposite strands. The synthesized strands contain randomly incorporated bases at positions corresponding to the mutated bases in the templates. The double-stranded mutagenized DNA is then used to transform the strain K38/pGP1-2, which is strain K38 containing the plasmid pGP1-2 (Tabor et al., supra). Upon heat induction this strain expresses T7 RNA polymerase. The transformed cells are plated at 30° C., with approximately 200 colonies per plate.

Screening for cells having T7 DNA polymerase lacking exonuclease activity is based upon the following finding. The 3' to 5' exonuclease of DNA polymerases serves a proofreading function. When bases are misincorporated, the exonuclease will remove the newly incorporated base which is recognized as "abnormal". This is the case for the analog of dATP, etheno-dATP, which is readily incorporated by T7 DNA polymerase in place of dATP. However, in the presence of the 3' to 5' exonuclease of T7 DNA polymerase, it is excised as rapidly as it is incorporated, resulting in no net DNA synthesis. As shown in FIG. 6, using the alternating copolymer poly d(AT) as a template, native T7 DNA polymerase catalyzes extensive DNA synthesis only in the presence of dATP, and not etheno-dATP. In contrast, modified T7 DNA polymerase, because of its lack of an associated exonuclease, stably incorporates etheno-dATP into DNA at a rate comparable to dATP. Thus, using poly d(AT) as a template, and dTTP and etheno-dATP as precursors, native T7 DNA polymerase is unable to synthesize DNA from this template, while T7 DNA polymerase which has lost its exonuclease activity will be able to use this template to synthesize DNA.

The procedure for lysing and screening large number of colonies is described in Raetz (72 Proc. Nat. Acad. Sci. 2274, 1975). Briefly, the K38/pGP1-2 cells transformed with the mutagenized gene 5-containing plasmids are transferred from the petri dish, where they are present at approximately 200 colonies per plate, to a piece of filter paper ("replica plating"). The filter paper discs are then placed at 42° C. for 60 min to induce the T7 RNA polymerase, which in turn expresses the gene 5 protein. Thioredoxin is constitutively produced from the chromosomal gene. Lysozyme is added to the filter paper to lyse the cells. After a freeze thaw step to ensure cell lysis, the filter paper discs are incubated with poly d(AT), [$\alpha^{32}$P]dTTP and etheno-dATP at 37° C. for 60 min. The filter paper discs are then washed with acid to remove the unincorporated [$^{32}$P]dATP. DNA will precipitate on the filter paper in acid, while nucleotides will be soluble. The washed filter paper is then used to expose X-ray film. Colonies which have induced an active T7 DNA polymerase which is deficient in its exonuclease will have incorporated acid-insoluble $^{32}P$, and will be visible by autoradiography. Colonies expressing native T7 DNA polymerase, or expressinq a T7 DNA polymerase defective in polymerase activity, will not appear on the autoradiograph.

Colonies which appear positive are recovered from the master petri dish containing the original colonies. Cells containing each potential positive clone will be induced on a larger scale (one liter) and T7 DNA polymerase purified from each preparation to ascertain the levels of exonuclease associated with each mutant. Those lacking exonuclease are appropriate for DNA sequencing.

DNA Sequencing Using Modified T7-type DNA Polymerase

DNA synthesis reactions using modified T7-type DNA polymerase result in chain-terminated fragments of uniform radioactive intensity, throughout the range of several bases to thousands of bases in length. There is virtually no background due to terminations at sites independent of chain terminating agent incorporation (i.e. at pause sites or secondary structure impediments).

Sequencing reactions using modified T7-type DNA polymerase consist of a pulse and chase. By pulse is meant that a short labelled DNA fragment is synthesized; by chase is meant that the short fragment is lengthened until a chain terminating agent is incorporated. The rationale for each step differs from conventional DNA sequencing reactions. In the pulse, the reaction is incubated at 0° C.-37° C. for 0.5-4 min in the presence of high levels of three nucleotide triphosphates (e.g., dGTP, dCTP and dTTP) and limiting levels of one other labelled, carrier-free, nucleotide triphosphate, e.g., [$^{35}$S] dATP. Under these conditions the modified polymerase is unable to exhibit its processive character, and a population of radioactive fragments will be synthesized ranging in size from a few bases to several hundred bases. The purpose of the pulse is to radioactively label each primer, incorporating maximal radioactivity while using minimal levels of radioactive nucleotides. In this, example, two conditions in the pulse reaction (low temperature, e.g., from 0°-20° C., and limiting levels of dATP, e.g., from 0.1 $\mu$M to 1 $\mu$M) prevent the modified T7-type DNA polymerase from exhibiting its processive character. Other essential environmental components of the mixture will have similar effects, e.g., limiting more than one nucleotide triphosphate. If the primer is already labelled (e.g., by kinasing) no pulse step is required.

In the chase, the reaction is incubated at 45° C. for 1-30 min in the presence of high levels (50-500 $\mu$M) of all four deoxynucleoside triphosphates and limiting levels (1-50 $\mu$M) of any one of the four chain terminating agents, e.g., dideoxynucleoside triphosphates, such that DNA synthesis is terminated after an average of 50-600 bases. The purpose of the chase is to extend each radioactively labeled primer under conditions of processive DNA synthesis, terminating each extension exclusively at correct sites in four separate reactions using each of the four dideoxynucleoside triphosphates. Two conditions of the chase (high temperature, e.g., from 30°-50° C.) and high levels (above 50 $\mu$M) of all four deoxynucleoside triphosphates) allow the modified T7-type DNA polymerase to exhibit its processive character for tens of thousands of bases; thus the same polymerase molecule will synthesize from the primer-template until a dideoxynucleotide is incorporated. At, a chase temperature of 45° C. synthesis occurs at >700 nucleotides/sec. Thus, for sequencing reactions the chase is complete in less than a second. ssb increases processivity, for example, when using dITP, or when using low temperatures, or low levels of triphosphates throughout the sequencing reaction.

Either [$\alpha^{35}$S]dATP, [$\alpha^{32}$P]dATP or fluorescently labelled nucleotides can be used in the DNA sequencing reactions with modified T7-type DNA polymerase. If an analog is fluorescent then end labelled primers are used, and no probe step is required.

Two components determine the average extensions of the synthesis reactions. First is the length of time of the pulse reaction. Since the pulse is done in the absence of chain terminating agents, the longer the pulse reaction time, the longer the primer extensions. At 0° C. the polymerase extensions average 10 nucleotides/sec. Second is the ratio of deoxynucleoside triphosphates to chain terminating agents in the chase reaction. A modified T7-type DNA polymerase does not discriminate against the incorporation of these analogs, thus the average length of extension in the chase is four times the ratio of the deoxynucleoside triphosphate concentration to the chain terminating agent concentration in the chase reaction. Thus, in order to shorten the average size of the extensions, the pulse time is shortened, e.g., to 30 sec. and the ratio of chain terminating agent to deoxynucleoside triphosphate concentration is raised in the chase reaction. This can be done either by raising the concentration of the chain terminating agent or lowering the concentration of deoxynucleoside triphosphate. To lengthen the average length of the extensions, the pulse time is increased, e.g., to 3-4 min, and the concentration of chain terminating agent is lowered (e.g., from 20 $\mu$M to 2 $\mu$M) in the chase reaction.

EXAMPLE 2: DNA SEQUENCING USING MODIFIED T7 DNA POLYMERASE

The following is an example of a sequencing protocol using dideoxy nucleotides as terminating agents.

9 $\mu$l of single-stranded M13 DNA (mGP1-2, prepared by standard procedures) at 0.7 mM concentration is mixed with 1 $\mu$l of complementary sequencing primer (standard universal 17-mer, 0.5 pmole primer / $\mu$l) and 2.5 $\mu$l 5×annealing buffer (200 mM Tris-HCl, pH 7.5, 50 mM MgCl$_2$) heated to 65° C. for 3 min, and slow cooled to room temperature over 30 min. In the pulse reaction, 12.5 $\mu$l of the above annealed mix was mixed with 1 $\mu$l dithiothreitol 0.1 M, 2 $\mu$l of 3 dNTPs (dGTP, dCTP, dTTP) 3 mM each (P.L Biochemicals, in TE), 2.5 $\mu$l [$\alpha^{35}$S]dATP, (1500 Ci/mmol, New England Nuclear) and 1 $\mu$l of modified T7 DNA polymerase described in Example 1 (0.4 mg/ml, 2500 units/ml, i.e. 0.4 $\mu$g, 2.5 units) and incubated at 0° C., for 2 min, after vortexing and centrifuging in a microfuge for 1 sec. The time of incubation can vary from 30 sec to 20 min and temperature can vary from 0° C. to 37° C. Longer times are used for sequencing sequences distant from the primer.

4.5 $\mu$l aliquots of the above pulse reaction are added to each of four tubes containing the chase mixes, preheated to 45° C. The four tubes, labeled G, A, T, C, each contain trace amounts of either dideoxy (dd) G, A, T, or C (P-L Biochemicals). The specific chase solutions are given below. Each tube contains 1.5 $\mu$l dATP 1mM, 0.5 $\mu$l 5× annealing buffer (200 mM Tris-HCl, pH 7.5, 50mM MgCl$_2$), and 1.0 $\mu$l ddNTP 100 $\mu$M (where ddNTP corresponds to ddG,A,T or C in the respective tubes). Each chase reaction is incubated at 45° C. (or 30° C.–50° C.) for 10 min, and then 6 μl of stop solution (90% formamide, 10mM EDTA, 0.1% xylenecyanol) added to each tube, and the tube placed on ice. The chase times can vary from 1–30 min.

The sequencing reactions are run on standard, 6% polyacrylamide sequencing gel in 7M urea, at 30 Watts for 6 hours. Prior to running on a gel the reactions are heated to 75° C. for 2 min. The gel is fixed in 10% acetic acid, 10% methanol, dried on a gel dryer, and exposed to Kodak OM1 high-contrast autoradiography film overnight.

EXAMPLE 3: DNA SEQUENCING USING LIMITING CONCENTRATIONS OF dNTPs

In this example DNA sequence analysis of mGP1-2 DNA is performed using limiting levels of all four deoxyribonucleoside triphosphates in the pulse reaction. This method has a number of advantages over the protocol in example 2. First, the pulse reaction runs to completion, whereas in the previous protocol it was necessary to interrupt a time course. As a consequence the reactions are easier to run. Second, with this method it is easier to control the extent of the elongations in the pulse, and so the efficiency of labeling of sequences near the primer (the first 50 bases) is increased approximately 10-fold.

7 μl of 0.75 mM single-stranded M13 DNA (mGP1-2) was mixed with 1 μl of complementary sequencing primer (17-mer, 0.5 pmole primer/μl) and 2 μl 5×annealing buffer (200 mM Tris-HCl pH 7.5, 50 mM MgCl$_2$, 250 mM NaCl) heated at 65° C. for 2 min, and slowly cooled to room temperature over 30 min. In the pulse reaction 10 μl of the above annealed mix was mixed with 1 μl dithiothreitol 0.1 M, 2 μl of 3 dNTPs (dGTP, dCTP, dTTP) 1.5 μM each, 0.5 μl [α$^{35}$S]-dATP, (1500 Ci/mmol, New England Nuclear) and 2 μl modified T7 DNA polymerase (0.1 mg/ml, 2000 units/ml, i.e., 0.2 μg, 2 units) and incubated at 37° C. for 5 min. (The temperature and time of incubation can be varied from 20° C.–45° C. and 1–60 min., respectively.)

3.5 μl aliquots of the above pulse reaction were added to each of four tubes containing the chase mixes, which were preheated to 37° C. The four tubes, labeled G, A, T, C, each contain trace amounts of either dideoxy G, A, T, C. The specific chase solutions are given below. Each tube contains 0.5 μl 5×annealing buffer (200 mM Tris-HCl pH 7.5, 50 mM MgCl$_2$, 250 mM NaCl), 1 μl 4dNTPs (dGTP, dATP, dTTP, dCTP) 200 μM each, and 1.0 μl ddNTP 20 μM. Each chase reaction is incubated at 37° C. for 5 min (or 20° C.–45° C. and 1–60 min respectively), and then 4 μl of a stop solution (95% formamide, 20 mM EDTA, 0.05% xylene-cyanol) added to each tube, and the tube placed on ice.

EXAMPLE 4: REPLACEMENT OF dGTP WITH dITP FOR DNA SEQUENCING

In order to sequence through regions of compression in DNA, i.e., regions having compact secondary structure, it is common to use dITP or deazaguanosine triphosphate (deaza GTP, Mizusawa et al., 14 Nuc. Acid Res. 1319, 1986, and Mills et al., 76 Proc. Natl. Acad. Sci. 2232, 1979) as a replacement for dGTP. We have found that both analogs function well with T7-type polymerases, especially with dITP in the presence of ssb. Preferably these reactions are performed with the above described genetically modified T7 polymerase, or the chase reaction is for 1–2 min., and/or at 20° C. to reduce exonuclease degradation.

Modified T7 DNA polymerase efficiently utilizes dITP or deaza-GTP in place of dGTP. dITP is substituted for dGTP in both the pulse and chase mixes at a concentration two to five times that at which dGTP is used. In the ddG chase mix ddGTP is still used (not ddITP).

The chase reactions using dITP are sensitive to the residual low levels (about 0.5 units) of exonuclease activity. To avoid this problem, the chase reaction times should not exceed 5 min when dITP is used. It is recommended that the four dITP reactions be run in conjunction with, rather than to the exclusion of, the four reactions using dGTP. If both dGTP and dITP are routinely used, the number of required mixes can be minimized by: (1) Leaving dGTP and dITP out of the chase mixes, which means that the four chase mixes can be used for both dGTP and dITP chase reactions. (2) Adding a high concentration of dGTP or dITP (2 μl at 0.5 mM and 1–2.5 mM respectively) to the appropriate pulse mix. The two pulse mixes then each contain a low concentration of dCTP,dTTP and [α$^{35}$S]dATP, and a high concentration of either dGTP or dITP. This modification does not adversely effect the quality of the sequencing reactions, and reduces the required number of pulse and chase mixes to run reactions using both dGTP and dITP to six.

The sequencing reaction is as for example 3, except that two of the pulse mixes contain (a) 3 dNTP mix for dGTP: 1.5 μM dCTP,dTTP, and 1 mM dGTP and (b) 3 dNTP mix for dITP: 1.5 μM dCTP,dTTP, and 2 mM dITP. In the chase reaction dGTP is removed from the chase mixes (i.e. the chase mixes contain 30 μM dATP,dTTP and dCTP, and one of the four dideoxynucleotides at 8 μM), and the chase time using dITP does not exceed 5 min.

Deposits

Strains K38/pGP5-5/pTrx-2, K38/pTrx-2 and M13 mGP1-2 have been deposited with the ATCC and assigned numbers 67,287, 67,286, and 40,303 respectively. These deposits were made on Jan. 13, 1989.

Applicants' and their assignees acknowledge their responsibility to replace these cultures should they die before the end of the term of a patent issued hereon, 5 years after the last request for a culture, or 30 years, whichever is the longer, and its responsibility to notify the depository of the issuance of such a patent, at which time the deposits will be made irrevocably available to the public and all restrictions to access to the cultures will be irrevocably removed. Until that time the deposits will be made available to the Commissioner of Patents under the terms of 37 CFR Section 1–14 and 35 USC Section 112.

OTHER EMBODIMENTS

Other embodiments are within the following claims.

Other uses of the modified DNA polymerases of this invention, which take advantage of their processivity, and lack of exonuclease activity, include the direct enzymatic amplification of genomic DNA sequences. This has been described, for other polymerases, by Saiki et al., 230 Science 1350, 1985; and Scharf, 233 Science 1076, 1986.

Referring to FIG. 6, enzymatic amplification of a specific DNA region entails the use of two primers which anneal to opposite strands of a double stranded DNA sequence in the region of interest, with their 3' ends directed toward one another (see dark arrows). The actual procedure involves multiple (10–40, preferably 16–20) cycles of denaturation, annealing, and DNA synthesis. Using this procedure it is possible to amplify a specific region of human genomic DNA over 200,000 times. As a result the specific gene fragment represents about one part in five, rather than the initial one part in a million. This greatly facilitates both the cloning and the direct analysis of genomic DNA. For diagnostic uses, it can speed up the analysis from several weeks to 1–2 days.

Unlike Klenow fragment, where the amplification process is limited to fragments under two hundred bases in length, modified T7-type DNA polymerases should (preferably in conjuction with *E. coli* DNA binding protein, or ssb, to prevent "snapback formation of double stranded DNA") permit the amplification of DNA fragments thousands of bases in length.

The modified T7-type DNA polymerases are also suitable in standard reaction mixtures: for (a) filling in 5' protruding termini of DNA fragments generated by restriction enzyme cleavage; in order to, for example, produce blunt-ended double stranded DNA from a linear DNA molecule having a single stranded region with no 3' protruding termini; (b) for labeling the 3' termini of restriction fragments, for mapping mRNA start sites, or sequencing DNA using the Maxam and Gilbert chemical modification procedure; and (c) for in vitro mutagenesis of cloned DNA fragments. For example, a chemically synthesized primer which contains specific mismatched bases is hybridized to a DNA template, and then extended by the modified T7-type DNA polymerase. In this way the mutation becomes permanently incorporated into the synthesized strand. It is advantageous for the polymerase to synthesize from the primer through the entire length of the DNA. This is most efficiently done using a processive DNA polymerase. Alternatively mutagenesis is performed by misincorporation during DNA synthesis (see above). This application is used to mutagenize specific regions of cloned DNA fragments. It is important that the enzyme used lack exonuclease activity. By standard reaction mixture is meant a buffered solution containing the polymerase and any necessary deoxynucleosides, or other compounds.

We claim:

1. A method of amplification of a DNA sequence comprising annealing a first and second primer to opposite strands of a double stranded DNA sequence and incubating the annealed mixture with a T7- type DNA polymerase having less than 500 units of exonuclease activity per mg of polymerase, wherein said first and second primers anneal to opposite strands of said DNA sequence with their 3' ends directed towards each other after annealing, and with the DNA sequence to be amplified located between the two annealed primers.

2. The method of claim 1 wherein said method further comprises, after said incubating step, denaturing the resulting DNA, annealing said first and second primers to said resulting DNA and incubating the annealed mixture with said polymerase.

3. The method of claim 2 wherein said steps of denaturing, then annealing and then incubating are repeated from 10 to 40 times.

4. The method of claim 1 wherein said exonuclease activity is less than 1 unit per mg of polymerase.

5. The method of claim 1, said T7- type DNA polymerase being selected from the group consisting of the DNA polymerases of phage T7, T3, Φ, ΦII, H, W31, gh-1, Y, A1122 and Sp6.

6. The method of claim 1 wherein said polymerase is non-discriminating for dideoxy nucleotide analogs.

7. The method of claim 1 wherein said polymerase is a modified polymerase having less than 50 units of exonuclease activity per mg of polymerase.

8. The method of claim 7 wherein said modified polymerase has less than 1 unit of activity per mg of polymerase.

9. The method of claim 7 wherein said modified polymerase has less than 0.1 unit of activity per mg of polymerase.

10. The method of claim 1 wherein said polymerase has no detectable exonuclease activity.

11. The method of claim 1 wherein said first and second primers include 10 bases or more.

12. The method of claim 1 wherein said first and second primers include 4 bases or more.

13. The method of claim 1 wherein said first and second primers comprise 4 to 20 bases.

14. The method of claim 1 wherein said polymerase is non-discriminating for nucleotide analogs and
said first and second primers are single-stranded RNA or DNA comprising 4–10 bases.

15. The method of claim 1 wherein said first and second primers are single stranded DNA or RNA.

16. A method of amplification of a DNA sequence comprising annealing a first and second primer to opposite strands of a double stranded DNA sequence and incubating the annealed mixture with a processive T7- type DNA polymerase, having less than 50% of the exonuclease activity of the naturally occurring level of exonuclease activity of said polymerase.

17. The method of claim 16 wherein said polymerase has less than 1% of the exonuclease activity of the naturally occurring level of exonuclease activity of said polymerase.

18. The method of claim 16 wherein said T7- type DNA polymerase is T7 DNA polymerase.

19. The method of claim 18 wherein said T7 DNA polymerase has less than 1% of the exonuclease activity of the naturally occurring level of exonuclease activity of said polymerase.

20. A method of amplification of a DNA sequence comprising annealing a first and second primer to opposite strands of a double stranded DNA sequence and incubating the annealed mixture with a processive T7- type DNA polymerase, said polymerase having a level of exonuclease activity which is sufficiently low to permit the nucleotide base sequence of the DNA molecule to be determined with said polymerase.

21. The method of claim 20 wherein said T7- type DNA polymerase is T7 DNA polymerase.

22. The method of claim 20 wherein said processive DNA polymerase has less than one percent of the exonuclease activity of the naturally occurring level of exonuclease activity of said polymerase.

23. The method of claim 22 wherein said polymerase has no detectable exonuclease activity.

24. The method of claim 22 or 23 wherein said polymerase is T7 DNA polymerase.

* * * * *